(12) United States Patent
Bonrad et al.

(10) Patent No.: US 10,326,090 B2
(45) Date of Patent: Jun. 18, 2019

(54) SEMICONDUCTOR COMPOSITION COMPRISING AN INORGANIC SEMICONDUCTING MATERIAL AND AN ORGANIC BINDER

(71) Applicant: Merck Patent GmbH, Darmstadt (DE)

(72) Inventors: Klaus Bonrad, Alsbach-Haehnlein (DE); Matthias Rehahn, Fuerth (DE); Nicole Kolmer-Anderl, Langenfeld (DE); Paul Mundt, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 15/515,323

(22) PCT Filed: Sep. 2, 2015

(86) PCT No.: PCT/EP2015/001769
§ 371 (c)(1),
(2) Date: Mar. 29, 2017

(87) PCT Pub. No.: WO2016/050335
PCT Pub. Date: Apr. 7, 2016

(65) Prior Publication Data
US 2017/0309848 A1    Oct. 26, 2017

(30) Foreign Application Priority Data

Sep. 30, 2014   (EP) ..................... 14003371

(51) Int. Cl.
*H01L 51/05*   (2006.01)
*H01L 51/00*   (2006.01)
(Continued)

(52) U.S. Cl.
CPC ........ *H01L 51/0566* (2013.01); *C07D 241/38* (2013.01); *C07D 487/04* (2013.01);
(Continued)

(58) Field of Classification Search
CPC ............. H01L 51/0566; H01L 51/0545; H01L 51/422; H01L 51/502; H01L 51/0072;
(Continued)

(56) References Cited

U.S. PATENT DOCUMENTS 5,892,244 A   4/1999  Tanaka et al.
5,998,804 A   12/1999 Suh et al.
(Continued)

FOREIGN PATENT DOCUMENTS

GB    2434918 A      8/2007
WO    2009/021663 A1 2/2009
WO    2012/000594 A1 1/2012

OTHER PUBLICATIONS

Machine Translation of WO 2009/021663 A1.*
(Continued)

*Primary Examiner* — William F Kraig
*Assistant Examiner* — Vicki B Booker
(74) *Attorney, Agent, or Firm* — Millen, White, Zelano and Branigan, P.C.

(57) ABSTRACT

The present invention relates to a semiconductor composition including an inorganic semiconducting material and an organic binder. The present invention further relates to an electronic device comprising a semiconducting layer consisting of such semiconductor composition.

20 Claims, 3 Drawing Sheets

(51) Int. Cl.
*C07D 241/38* (2006.01)
*C07D 487/04* (2006.01)
*H01L 51/42* (2006.01)
*H01L 51/50* (2006.01)

(52) U.S. Cl.
CPC ...... *H01L 51/0007* (2013.01); *H01L 51/0072* (2013.01); *H01L 51/0545* (2013.01); *H01L 51/422* (2013.01); *H01L 51/502* (2013.01); *H01L 51/4233* (2013.01)

(58) Field of Classification Search
CPC .. H01L 51/0007; C07D 487/04; C07D 241/38
See application file for complete search history.

(56) References Cited

U.S. PATENT DOCUMENTS

| | | | |
|---|---|---|---|
| 6,723,394 | B1 | 4/2004 | Sirringhaus et al. |
| 7,800,103 | B2 | 9/2010 | Katakura et al. |
| 9,117,964 | B2 | 8/2015 | Deshmukh et al. |
| 2005/0003232 | A1 | 1/2005 | Shitagaki et al. |
| 2007/0102696 | A1 | 5/2007 | Brown et al. |
| 2008/0121873 | A1 | 5/2008 | Katakura et al. |
| 2012/0091448 | A1* | 4/2012 | Ueno .................... H01L 51/506 257/40 |
| 2013/0102108 | A1 | 4/2013 | Deshmukh et al. |

OTHER PUBLICATIONS

International Search Report dated Dec. 3, 2015 issued in corresponding PCT/EP2015/001769 application (3 pages).
Written Opinion of the International Searching Authority dated Dec. 3, 2015 issued in corresponding PCT/EP2015/001769 application (5 pages).
B. Sun et al., "Low-Temperature Sintering of In-Plane Self-Assembled ZnO Nanorods for Solution-Processed High-Performance Thin Film Transistors", The Journal of Physical Chemistry C, vol. 111 (2007) pp. 18831-18835.
B. Bubel et al., "N-Type Perylene to Fill Voids in Solution Processed Nanoparticulate Zinc Oxide Thin Films", Physica E, vol. 44 (2012) pp. 2124-2127.
M.C. Clark, "Chemistry of Indanthrone. Part X. 7,16-Dihydrodinaphtho[2,3-b:2',3'-i]phenazine-5,9,14,18-diquinone: A Linear Isomer of Indanthrone", J. Chem. Soc. C, (1966) pp. 277-283.
E. Leete et al., "Linear Indanthrone and Related Phenazines", J. Org. Chem., vol. 31 (1966) pp. 3734-3739.
A.M. Amer et al., "On the Synthesis of Pyrazino[2,3-b]phenazine and 1H-Imidazo[4,5-b]phenazine Derivatives", Monatshefte fur Chemie, vol. 130 (1999) pp. 1217-1225.
H. Wang et al., "Fused-Ring Pyrazine Derivatives for n-Type Field-Effect Transistors", Applied Materials & Interfaces, vol. 1, No. 5 (2009) pp. 1122-1129.
H.E. Gottlieb et al., "Nmr Chemical Shifts of Common Laboratory Solvents as Trace Impurities", J. Org. Chem., vol. 62, No. 21 (1997) pp. 7512-7515.
C.M. Cardona et al., "Electrochemical Considerations for Determining Absolute Frontier Orbital Energy Levels of conjugated Polymers for Solar Cell Applications", Advanced Materials, vol. 23 (2011) pp. 2367-2371.
D.M. De Leeuw et al., "Stability of N-Type Doped Conducting Polymers and Consequences for Polymeric Microelectronic Devices", Synthetic Metals, vol. 87 (1997) pp. 53-59.
Y. Li et al., "Electrochemical Properties of Luminescent Polymers and Polymer Light-Emitting Electrochemical Cells", Synthetic Metals, vol. 99 (1999) pp. 243-248.

* cited by examiner

SEMICONDUCTOR COMPOSITION COMPRISING AN INORGANIC SEMICONDUCTING MATERIAL AND AN ORGANIC BINDER

TECHNICAL FIELD

The present invention relates to a semiconductor composition comprising an inorganic semiconducting material and an organic binder. The present invention further relates to an electronic device comprising a semiconducting layer consisting of such semiconductor composition.

BACKGROUND AND DESCRIPTION OF THE PRIOR ART

Inorganic semiconducting materials, for example semiconducting metal oxides, have found widespread use in the electronic industry, for example in thin film transistors (TFTs). To obtain semiconducting layers of acceptable charge mobility it has proven advantageous to deposit the inorganic semiconducting materials onto a supporting layer by means of vapor gas phase deposition methods. These methods, however, require high vacuum and frequently also necessitate a thermal post-treatment to further improve the charge mobility of the semiconducting layer.

Without wishing to be bound by theory it may be that the limited charge mobility directly following deposition is due to the particulate nature of the inorganic semiconducting materials. Charges are quickly transported within a particle of the inorganic semiconducting material but are slowed down when having to "jump" from one particle to the next. It is believed that thermal post-treatment (or "sintering") increases the particle sizes and therefore decreases the number of interfaces between particles.

However, gas phase deposition methods are not well suited for industrial production of large area coatings. For mass production, industry is therefore turning to other deposition methods, such as for example various printing methods as for example ink-jet printing. For inorganic semiconducting materials their limited solubility has proven to be a major drawback, which may potentially be avoided for example by applying a soluble inorganic precursor, for example a soluble metal complex, which is then converted into the respective semiconducting compound, or by applying a metal compound particle dispersion. In either method the applied layer, either of the soluble inorganic precursor or the metal compound particle dispersion, needs to be heated, so as to convert the precursor into the semiconductor compound and sinter the particles. The precursor conversion generally requires temperatures of around 300° C., thus rendering this method unsuitable to be used with many polymeric substrates, which are of interest particularly for flexible and/or light-weight electronic devices.

Examples of soluble inorganic precursors are zinc acetate, as for example disclosed in B. Sun et al., J. Phys. Chem. C, 2007, 111, 18831-18835, and zinc oximates as for example disclosed in WO 2012/000594 A1. As discussed in B. Sun et al., J. Phys. Chem. C, 2007, 111, 18831-18835 these precursors require heating to at least 250° C. in order to convert them into the inorganic semiconductor material and to remove any organic residues as well.

An example of a composition comprising zinc oxide nanoparticles and perylene di-imides is disclosed in S. Bubel et al., Physica E 44 (2012) 2124-2127. However, the resulting transistors were characterized by very low charge carrier mobility of $7.5 \cdot 10^{-5}$ $cm^2$ $V^{-1}$ $s^{-1}$ and an $I_{on}/I_{off}$ ratio of $10^3$.

Consequently there is a need for a composition and/or a process that would avoid the drawbacks of the existing compositions and processes and would particularly allow to work at lower temperatures than in known methods.

It is therefore an object of the present application to provide a semiconductor composition and/or a process allowing the production of a semiconducting layer at reduced temperatures.

It is also an object of the present application to provide a semiconductor composition and/or a process allowing the production of a semiconducting layer having good semiconducting properties.

It is a further object of the present application to provide a semiconductor composition and/or a process allowing simplified production of electronic devices.

Additional objects of the present application become evident from the following description as well as the examples.

SUMMARY OF THE INVENTION

The present inventors have now surprisingly found that the above objects may be attained either individually or in any combination by the semiconductor composition and the process of the present application.

The present application therefore provides for a semiconductor composition comprising an inorganic semiconducting material and an organic binder, said organic binder being of formula (I)

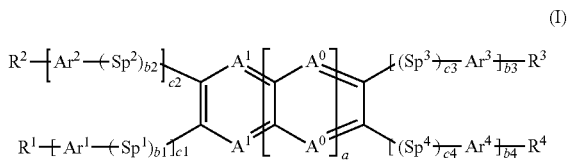

with
a being at each occurrence independently of any other an integer selected from the group consisting of 1, 2, 3, 4, 5, 6 and 7,
$A^0$ and $A^1$ being at each occurrence independently of each other either C—$R^5$ or N, provided that at least one of the $A^0$ and $A^1$ is N,
b1, b2, b3, b4, c1, c2, c3 and c4 each being at each occurrence independently of the other 0 or 1,
$Sp^1$, $Sp^2$, $Sp^3$ and $Sp^4$ being at each occurrence independently of the other selected from the group consisting of consisting of formulae (III-a) to (III-h)

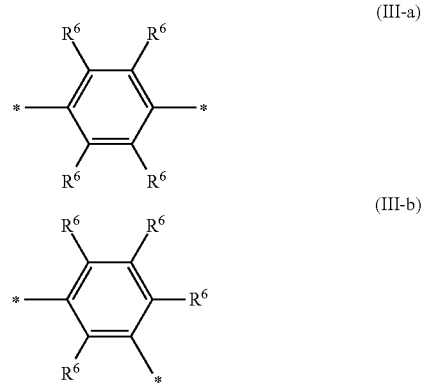

-continued

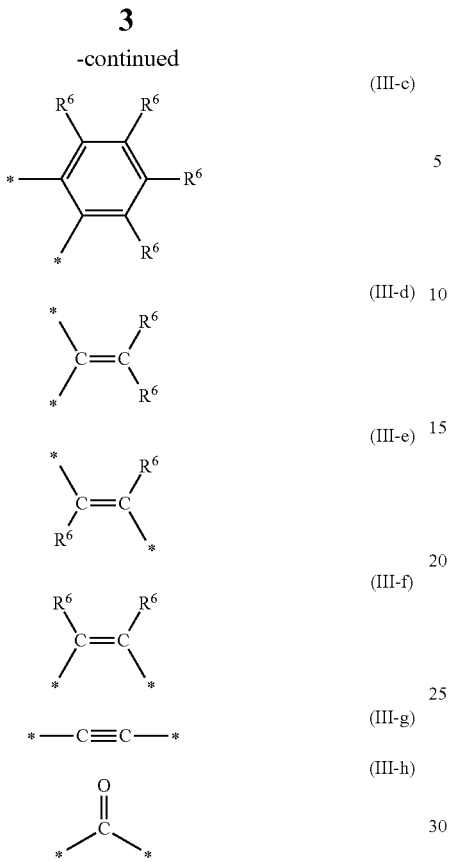

Ar¹, Ar², Ar³ and Ar⁴ being at each occurrence independently of the other selected from formula (II), with * denoting the respective bonds to the respective group Sp¹, Sp², Sp³ or Sp⁴ or—if such is not present—to the central unit of formula (II), to the respective group R¹, R², R³ or R⁴ and to substituents R⁷ and R⁸;

R¹, R², R³, R⁴ and—if present—R⁵ and R⁶ being at each occurrence independently of each other a group $R^A$ or a group $R^B$, provided that at least one of R¹, R², R³, R⁴ and—if present—R⁵ and R⁶ is a group $R^A$.

$R^A$ being at each occurrence independently selected from the group consisting of
(i) H, F, Br, Cl, —CN, —CH₂Br, —CH₂OR⁰, —NC, —NCO, —NCS, —OCN, —SCN, —C(O)NR⁰R⁰⁰, —C(O)X⁰, —C(O)R⁰, —C(O)R⁰—OR⁰⁰, —NR⁰R⁰⁰, —PR⁰R⁰⁰, —O—P(OR⁰)(OR⁰⁰), —O—PH(O)—OR⁰, —SH, —SR⁰, —S(O)R⁰, —SO₃H, —SO₂R⁰, —SO₃R⁰, —NO₂, —SF₅, —C≡C—R⁰, —CR⁰=CR⁰⁰R⁰⁰⁰,
(ii) fluorinated alkyl having from 1 to 40 carbon atoms,
(iii) alkyl or fluorinated alkyl having from 1 to 40 carbon atoms, wherein two adjacent carbon atoms are replaced by —CR⁰=CR⁰⁰— or —C≡C—,
(iv) alkyl or fluorinated alkyl having from 1 to 40 carbon atoms, wherein one or more, preferably non-adjacent, carbon atoms are replaced by a heteroatom or heteroatom group,
(v) aryl having from 6 to 30 carbon ring atoms,
(vi) heteroaryl having from 5 to 30 ring atoms,
wherein said aryl and heteroaryl may be unsubstituted or substituted with one or more groups $R^S$, and wherein said alkyl and fluorinated alkyl may be substituted with one or more groups selected from the group consisting of $R^S$, aryl as defined herein and heteroaryl, $R^B$ being at each occurrence independently selected from the group consisting of
(i) H, —SiR⁰R⁰⁰R⁰⁰⁰,
(ii) alkyl having from 1 to 40 carbon atoms,
(iii) alkoxy having from 1 to 39 carbon atoms,
(iv) —(CH₂)_d—R⁹, wherein d is an integer of from 1 to 5 and R⁹ is selected from the group consisting of
  (a) —SiR⁰R⁰⁰R⁰⁰⁰, —C≡C—SiR⁰R⁰⁰R⁰⁰⁰,
  (b) alkyl having from 1 to 19 carbon atoms,
  (c) alkyl having from 1 to 19 carbon atoms, wherein two adjacent carbon atoms are replaced by —CR⁰=CR⁰⁰— or —C≡C—,
  (d) alkyl having from 1 to 19 carbon atoms, wherein one or more, preferably non-adjacent, carbon atoms are replaced by a heteroatom or heteroatom group as defined herein,
  (e) aryl having from 6 to 30 carbon ring atoms, and
  (f) heteroaryl having from 5 to 30 ring atoms,
wherein said aryl and heteroaryl may be unsubstituted or substituted with one or more groups $R^S$, and wherein said alkyl and fluorinated alkyl may be substituted with one or more groups selected from the group consisting of $R^S$, aryl and heteroaryl, R⁰, R⁰⁰ and R⁰⁰⁰ being at each occurrence independently of each other selected from the group consisting of H, F, $C_{1-40}$ organyl or organoheteryl, and substituted $C_{1-40}$ organyl or organoheteryl, X⁰ being at each occurrence independently selected from the group consisting of F, Cl, Br and I, $R^S$ being at each occurrence independently selected from the group consisting of alkyl having from 1 to 30 carbon atoms, halogenated alkyl having from 1 to 30 carbon atoms, aryl having from 6 to 30 carbon ring atoms, aryl having from 6 to 30 carbon ring atoms substituted with at least one group independently selected from the group consisting of F, Cl, Br, I, alkyl having from 1 to 30 carbon atoms and halogenated alkyl having from 1 to 30 carbon atoms, heteroaryl having from 1 to 30 ring atoms, heteroaryl having from 1 to 30 ring atoms substituted with at least one group independently selected from the group consisting of F, Cl, Br, I, alkyl having from 1 to 30 carbon atoms and halogenated alkyl having from 1 to 30 carbon atoms.

The present application therefore also provides for a process for the production of an organic electronic device, said process comprising the steps of
(A-i) providing a dispersion of an inorganic semiconducting nanoparticle material as defined herein in a dispersant as defined herein;
(A-ii) applying said dispersion to a substrate;
(A-iii) removing said dispersant, thus obtaining a layer of an inorganic semiconducting nanoparticles material;
(A-iv) providing a solution of an organic binder as defined herein in a solvent as defined herein;

(A-v) applying said solution to the layer of an inorganic semiconducting nanoparticle material obtained in step (A-iii); and
(A-vi) removing said solvent,
or said process comprising the steps of
(B-i) mixing an inorganic semiconducting nanoparticles material as defined herein, an organic binder as defined herein and a solvent to obtain a semiconductor formulation;
(B-ii) applying said semiconductor formulation to a substrate; and
(B-iii) removing said solvent,
to obtain a semiconducting layer consisting of the present semiconductor composition.

DETAILED DESCRIPTION OF THE INVENTION

Figure 1:
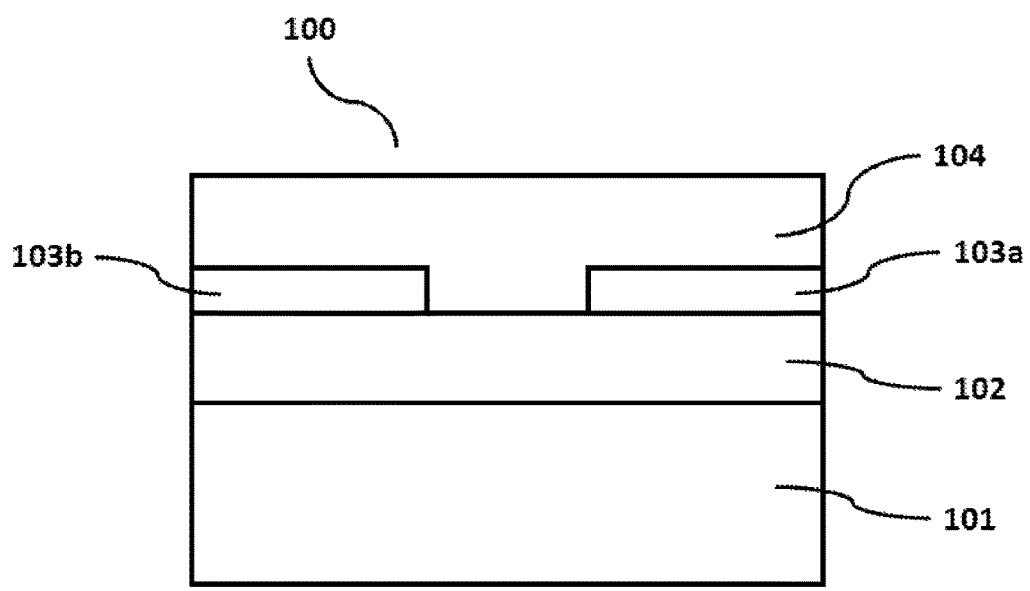
FIG. 1 is an exemplary schematic representation of the thin film transistors (TFTs) of Example 19 and Example 20.

As used herein "Me" may denote methyl, "Ph" phenyl and "THF" tetrahydrofuran.

As used herein the term "fusion atom" denotes any atom of a fused ring system which is common to two or more rings (see Pure & Appl. Chem., Vol. 70, No. 1, pp. 143-216, 1988, particularly page 147).

As used herein the term "fluorinated", which includes "perfluorinated", denotes replacement of one or more hydrogen atoms with the respective number of fluorine atoms. The term "perfluorinated" is used to indicate that all hydrogen atoms are replaced by fluorine.

As used herein the term "halogenated" denotes replacement of one or more hydrogen atoms with the respective number of halogen atoms, e.g. F, Cl, Br and I.

As used herein the term "organic electronic device" denotes an electronic device comprising an organic compound.

As used herein the term "n-type" or "n-type semiconductor" will be understood to mean an extrinsic semiconductor in which the conduction electron density is in excess of the mobile hole density, and the term "p-type" or "p-type semiconductor" will be understood to mean an extrinsic semiconductor in which mobile hole density is in excess of the conduction electron density (see also J. Thewlis, Concise Dictionary of Physics, Pergamon Press, Oxford, 1973).

In general terms the present application relates to a semiconductor composition comprising an inorganic semiconducting material as defined herein and an organic binder as defined herein. The present application further relates to an organic electronic device comprising a semiconducting layer consisting of said semiconductor composition.

With regards to the total weight of such semiconductor composition it is preferred that the present inorganic semiconductor composition comprises said inorganic semiconducting material and said organic binder in at least 50 wt %, more preferably in at least 60 wt % or 70 wt %, even more preferably in at least 80 wt % or 90 wt %, still even more preferably in at least 95 wt % or 97 wt % or 99 wt % or 99.5 wt % or 99.9 wt %, and most preferably consists of said inorganic semiconducting material and said organic binder, with wt % relating to the total weight of said semiconductor composition.

Said semiconductor composition preferably comprises said inorganic semiconducting material and said organic binder in a weight ratio of 20:1 to 1:20, more preferably of 15:1 to 1:15, even more preferably of 10:1 to 1:10, still even more preferably of 5:1 to 1:5 or 4:1 to 1:4 or 3:1 to 1:3, and most preferably 2:1 to 1:2.

Inorganic Semiconducting Material

For the purposes of the present invention the type of semiconducting material is not very limited. It is, however, preferred that such semiconducting material is available in form of nanoparticles, i.e. is an inorganic semiconducting nanoparticle material.

Said nanoparticles have a diameter of preferably at least 1 nm, more preferably at least 5 nm, even more preferably at least 10 nm and most preferably at least 15 nm.

Said nanoparticles have a diameter of preferably at most 100 nm, more preferably at most 90 nm, even more preferably at most 80 nm and most preferably at most 70 nm.

In case that the nanoparticles are not of spherical shape, the length or the diameter or both may be selected as indicated above in respect to the diameter.

Said inorganic semiconducting material is preferably selected from the group consisting of metal oxides, metal sulfides, metal selenides and metal tellurides. More preferably it is selected from the group consisting of metal oxides. Even more preferably it is selected from the group consisting of $ZnO$, $SnO_2$, $In_2O_3$ and $Cu_2O$. Still even more preferably it is $ZnO$ or $SnO_2$. Most preferably it is $ZnO$.

Preferably, said inorganic semiconducting material has a content of organic residues of at most 8 wt %, more preferably of at most 7 wt %, even more preferably of at most 6 wt %, still even more preferably of at most 5 wt % and most preferably of at most 4.5 wt %, relative to the total weight of the inorganic semiconducting material. The content of organic residues is determined by thermogravimetric analysis (TGA) as described in detail in the test methods.

For practical limitations the inorganic semiconducting material generally has a content of organic residues of at least 0.1 wt % or 0.5 wt % or 1.0 wt %, relative to the total weight of the inorganic semiconducting material.

Without wishing to be bound by theory it is believed that the low level of organic residues, which for inorganic semiconducting particles produced from the respective precursors comprising organic components is surprisingly low, helps in improving the semiconducting properties of the nanoparticles and consequently of the semiconducting layer in the electronic device.

The present inorganic semiconducting nanoparticle material may be dispersed in a suitable dispersant. Said dispersant may be any solvent, preferably organic solvent, suitable for dispersing the present inorganic semiconducting nanoparticle material as well as allowing for deposition of such dispersion onto a substrate when producing an organic electronic device.

Suitable dispersants may generally be selected from the solvents defined in the following in respect to the solution of the organic binder. It is, however, preferred that the dispersant is selected from the group consisting of water, alcohols, ethers, haloalkanes and any mixture of these.

Said dispersant and said solvent may be the same or different. It is, however, preferred that they are the same.

Examples of alcohols suited as dispersant may be selected from the group consisting of methanol, ethanol, n-propanol, iso-propanol and 2-methoxyethanol, with methanol and 2-methoxyethanol being preferred.

Examples of ethers suited as dispersant may be selected from the group consisting of dibutylether, tetrahydrofuran and dioxin, with tetrahydrofuran preferred.

Examples of haloalkanes suited as dispersant may be selected from the group consisting of chloroform and dichloromethane ($CH_2Cl_2$), with dichloromethane being preferred.

Organic Binder

The present organic binder is of the following formula (I)

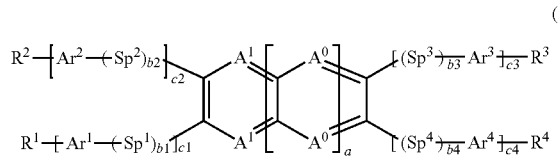

(I)

with $A^0$, $A^1$, $A^1$, $R^1$, $R^2$, $R^3$, $R^4$, $Ar^1$, $Ar^2$, $Ar^3$, $Ar^4$, $Sp^1$, $Sp^2$, $Sp^3$, $Sp^4$, a, b1, b2, b3, b4, c1, c2, c3 and c4 as defined herein.

For ease of reference, the central unit having the following formula (II)

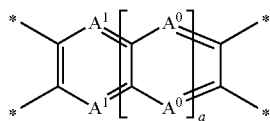

(II)

of the organic binder of formula (I) will herein generally be referred to as "central unit of formula (II)".

a is an integer selected from the group consisting of 1, 2, 3, 4, 5, 6 and 7. Preferably, a is an integer selected from the group consisting of 1, 2, 3, 4, 5 and 6. More preferably, a is an integer selected from the group consisting of 1, 2, 3, 4 and 5. Even more preferably, a is an integer selected from the group consisting of 1, 2, 3 and 4. Most preferably, a is 2 or 3.

Examples of such a central unit of formula (II) may independently of each other be selected from the group consisting of formulae (II-a) to (II-e)

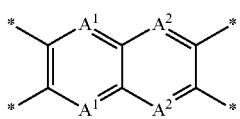

(II-a)

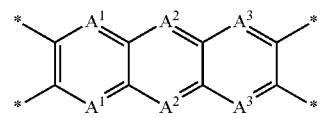

(II-b)

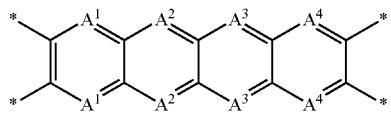

(II-c)

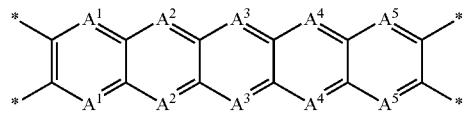

(II-d)

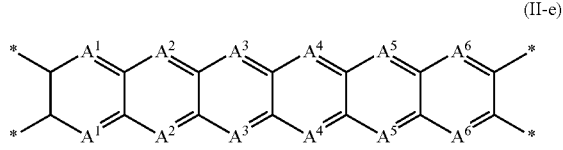

(II-e)

with $A^1$, $A^2$, $A^3$, $A^4$, $A^5$ and $A^6$ as defined herein.

$A^0$ and $A^1$ are at each occurrence independently of each other either C—$R^5$ or N, provided that at least one, preferably at least two, of the $A^0$ and $A^1$ is (are) N, with $R^5$ as defined herein.

The $A^0$ or $A^1$ in the same aromatic ring of formula (I) and formulae (II-a) to (II-de) and any subformulae of these may be the same or different. Preferably they are the same, i.e. both $A^0$ or $A^1$ in the same ring are C—$R^5$, preferably with the two $R^5$ being the same as well, or both are N.

Of formulae (II-a) to (II-e), formulae (II-b) and (II-c) are preferred. Suitable examples of formulae (II-b) and (II-c) may be selected from the group consisting of following formulae (II-b-1), (II-b-2) and (II-c-1) to (II-c-3)

| Formula | $A^1$ | $A^2$ | $A^3$ | $A^4$ |
|---|---|---|---|---|
| (II-b-1) | C-$R^5$ | N | C-$R^5$ | — |
| (II-b-2) | N | C-$R^5$ | N | — |
| (II-c-1) | C-$R^5$ | C-$R^5$ | C-$R^5$ | N |
| (II-c-2) | C-$R^5$ | N | C-$R^5$ | N |
| (II-c-3) | N | C-$R^5$ | N | C-$R^5$ | with $R^5$ as defined herein.

Examples of an organic binder of formula (I) may be selected from the group consisting of the following formulae (I-a) to (I-e)

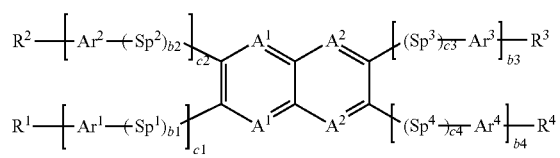

(I-a)

-continued

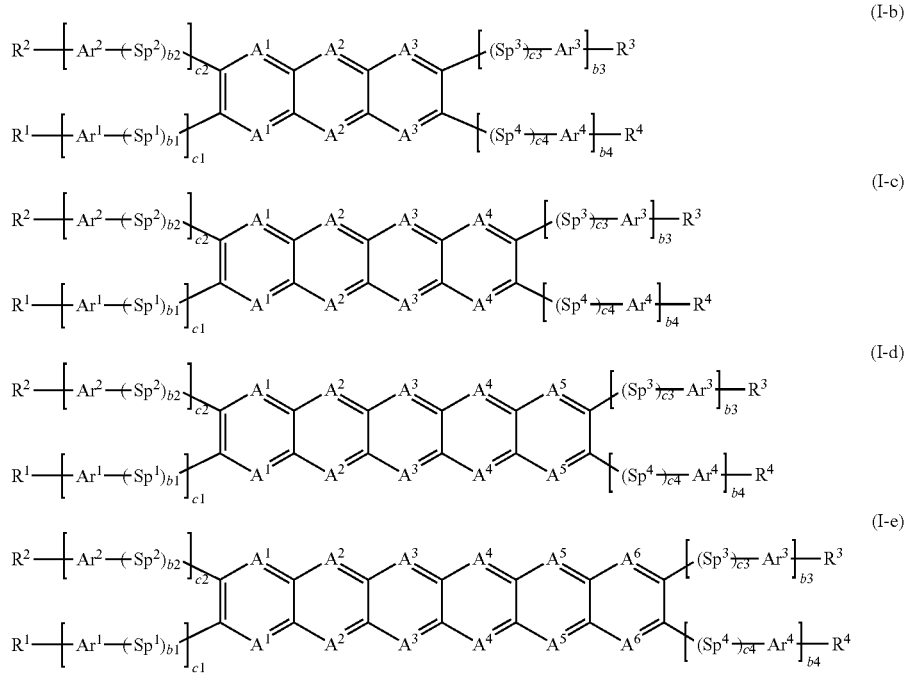

with $A^1$, $A^2$, $A^3$, $A^4$, $A^5$, $A^6$, $R^1$, $R^2$, $R^3$, $R^4$, $Ar^1$, $Ar^2$, $Ar^3$, $Ar^4$, $Sp^1$, $Sp^2$, $Sp^3$, $Sp^4$, a, b1, b2, b3, b4, c1, c2, c3 and c4 as defined herein.

$A^1$, $A^2$, $A^3$, $A^4$, $A^5$ and $A^6$ are at each occurrence independently of each other either C—$R^5$ or N, provided that at least one, preferably at least two, of the $A^1$, $A^2$, $A^3$, $A^4$, $A^5$ and $A^6$ is (are) N, with $R^5$ as defined herein.

The respective groups $A^1$, $A^2$, $A^3$, $A^4$, $A^5$ and $A^6$ bound to the same fusion atom may be the same or different. Preferably they are different, i.e. one of the respective $A^1$, $A^2$, $A^3$, $A^4$, $A^5$ and $A^6$ bound to the same fusion atom is C—$R^5$, the other is N.

In formulae (I-a) and (II-a) preferably at least one of, most preferably both $A^2$ may be N. In formulae (I-b) and (II-b) preferably at least one of, most preferably both $A^3$ may be N. In formulae (I-c) and (II-c) preferably at least one of, most preferably both $A^4$ may be N. In formulae (I-d) and (II-d) preferably at least one of, most preferably both $A^5$ may be N. In formulae (I-e) and (II-e) preferably at least one of, most preferably both $A^6$ may be N.

Of formulae (I-a) to (I-e), formulae (I-b) and (I-c) are preferred. Suitable examples of formulae (I-b) and (I-c) may be selected from the group consisting of following formulae (I-b-1), (I-b-2) and (I-c-1) to (I-c-3)

| Formula | $A^1$ | $A^2$ | $A^3$ | $A^4$ |
|---|---|---|---|---|
| (I-b-1) | C-$R^5$ | N | C-$R^5$ | — |
| (I-b-2) | N | C-$R^5$ | N | — |
| (I-c-1) | C-$R^5$ | C-$R^5$ | C-$R^5$ | N |
| (I-c-2) | C-$R^5$ | N | C-$R^5$ | N |
| (I-c-3) | N | C-$R^5$ | N | C-$R^5$ | with $R^5$ as defined herein.

Each of b1, b2, b3 and b4 may independently of the other be 0 or 1. For example, one or two or three or all four of b1, b2, b3 and b4 may be identical and be 0 or 1.

Each of c1, c2, c3 and c4 may independently of the other be 0 or 1. For example, one or two or three or all four of c1, c2, c3 and c4 may be identical and be 0 or 1.

Preferably b1, b2, b3, b4 c1, c2, c3 and c4 are selected such that one or more, for example two, three or even four, of the following conditions are met, provided that they are not mutually exclusive (i) b1 and c1 are identical and are 0 or 1,
(ii) b2 and c2 are identical and are 0 or 1,
(iii) b3 and c3 are identical and are 0 or 1,
(iv) b4 and c4 are identical and are 0 or 1, and
(v) the sum of c1, c2, c3 and c4 (i.e. c1+c2+c3+c4) is preferably at most 3, more preferably at most 2, even more preferably at most 1, and most preferably is 0.

It is also preferred that if any one or more of c1, c2, c3 and c4 is 1 then the respective of b1, b2, b3 and b4 is 1 as well.

$Sp^1$, $Sp^2$, $Sp^3$ and $Sp^4$ are at each occurrence independently selected from the group consisting of formulae (III-a) to (III-h)

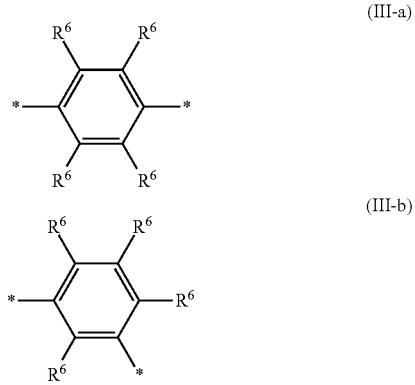

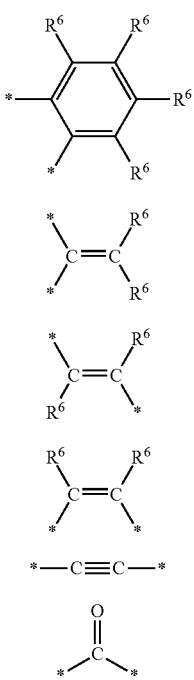

(III-c)

(III-d)

(III-e)

(III-f)

(III-g)

*—C≡C—*

(III-h)

with $R^6$ as defined herein and the asterisk "*" denoting the respective bonds to the central unit of formula (II) on one and to the respective group $Ar^1$, $Ar^2$, $Ar^3$ or $Ar^4$ on the other.

$R^6$ may at each occurrence independently of the other be a group $R^A$, a group $R^B$ or a group $R^S$. Preferably $R^6$ is H or F.

Preferably $Sp^1$, $Sp^2$, $Sp^3$ and $Sp^4$ are at each occurrence independently selected from the groups consisting of formulae (III-a), (III-e) and (III-g). Particularly preferred is formula (III-a).

$Ar^1$, $Ar^2$, $Ar^3$ and $Ar^4$ are at each occurrence independently of the other selected from formula (II) with $A^0$, $A^1$ and a as defined herein and the asterisks "*" denoting the respective bonds to the respective group Sp" (with n=1, 2, 3, or 4) or—if such is not present—to the central unit of formula (II), to the respective group R" (with n=1, 2, 3, or 4) and to substituents $R^7$ and $R^8$ as defined herein. If more than one of $Ar^1$, $Ar^2$, $Ar^3$ and $Ar^4$ is present in the organic binder of formula (I) they may be the same or differ from one another in the selection of any one or more of $A^0$, $A^1$ and a.

Preferred examples of $Ar^1$, $Ar^2$, $Ar^3$ and $Ar^4$ may at each occurrence independently of the other be selected from the group consisting of formulae (IV-a), (IV-b) and (IV-c)

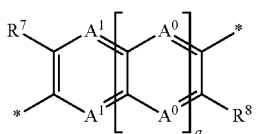

(IV-a)

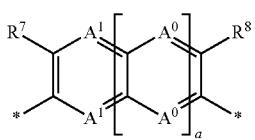

(IV-b)

(IV-c)

with $A^0$, $A^1$, a, $R^7$ and $R^8$ as defined herein and the asterisks "*" denoting the respective bonds to the respective group Sp" (with n=1, 2, 3, or 4) or—if such is not present—to the central unit of formula (II), and to the respective group R" (with n=1, 2, 3, or 4).

$R^1$, $R^2$, $R^3$, $R^4$ and—if present—$R^5$, $R^2$ and $R^8$ are at each occurrence independently of each other a group $R^A$ or a group $R^B$, provided that at least one, preferably at least two, of $R^1$, $R^2$, $R^3$, $R^4$ and—if present—$R^5$, $R^7$ and $R^8$ is a group $R^A$.

Preferably $R^1$, $R^2$ and $R^5$ are at each occurrence independently of each other a group $R^A$, and $R^3$ and $R^4$ are independently of each other a group $R^B$. More preferably, $R^1$, $R^2$ and $R^5$ are identical and are a group $R^A$, and $R^3$ and $R^4$ are identical and are a group $R^B$. Preferably one of $R^7$ and $R^8$ is a group $R^A$, while the other is a group $R^B$.

$R^A$ may be selected from the group consisting of (i) H, F, Br, Cl, —CN, —$CH_2Br$, —$CH_2OR^0$, —NC, —NCO, —NCS, —OCN, —SCN, —$C(O)NR^0R^{00}$, —$C(O)X^0$, —$C(O)R^0$, —$C(O)R^0$—$OR^{00}$, —$NR^0R^{00}$, —$PR^0R^{00}$, —O—$P(OR^0)(OR^{00})$, —O—PH(O)—$OR^0$, —SH, —$SR^0$, —$S(O)R^0$, —$SO_3H$, —$SO_2R^0$, —$SO_3R^0$, —$NO_2$, —$SF_5$, —C≡C—$R^0$, —$CR^0$=$CR^{00}R^{000}$; preferably F, Br, Cl, —CN, —$CH_2Br$, —$CH_2OR^0$, —NC, —NCO, —NCS, —OCN, —SCN, —$C(O)NR^0R^{00}$, —$C(O)X^0$, —C(O)$R^0$, —$C(O)R^0OR^{00}$, —$NR^0R^{00}$, —$PR^0R^{00}$, —O—P$(OR^0)(OR^{00})$, —O—PH(O)—$OR^0$, —SH, —$SR^0$, —$S(O)R^0$, —$SO_3H$, —$SO_2R^0$, —$SO_3R^0$, —$NO_2$, —$SF_5$, —C≡C—$R^0$, —$CR^0$=$CR^{00}R^{000}$, (ii) fluorinated alkyl having from 1 to 40, preferably from 1 to 30, more preferably from 1 to 20, even more preferably from 1 to 10 and most preferably from 1 to 5 carbon atoms, (iii) alkyl or fluorinated alkyl having from 1 to 40, preferably from 1 to 30, more preferably from 1 to 20, even more preferably from 1 to 10 and most preferably from 1 to 5 carbon atoms, wherein two adjacent carbon atoms are replaced by —$CR^0$=$CR^{00}$— or —C≡C—, (iv) alkyl or fluorinated alkyl having from 1 to 40, preferably from 1 to 30, more preferably from 1 to 20, even more preferably from 1 to 10 and most preferably from 1 to 5 carbon atoms, wherein one or more, preferably non-adjacent, carbon atoms are replaced by a heteroatom or heteroatom group as defined herein, (v) aryl having from 6 to 30, preferably from 6 to 18, carbon ring atoms, (vi) heteroaryl having from 5 to 30 ring atoms, with $R^0$, $R^{00}$, $R^{000}$ and $X^0$ as defined herein, wherein said aryl and heteroaryl may be unsubstituted or substituted with one or more groups $R^S$, and wherein said alkyl and fluorinated alkyl may be substituted with one or more groups selected from the group consisting of $R^S$, aryl as defined herein and heteroaryl as defined herein.

Preferred examples of $R^A$ are F and fluorinated alkyl.

$R^B$ may be selected from the group consisting of
(i) H, —SiR$^O$R$^{OO}$R$^{OOO}$,
(ii) alkyl having from 1 to 40, preferably from 1 to 30, more preferably from 1 to 20, even more preferably from 1 to 10 and most preferably from 1 to 5 carbon atoms,
(iii) alkoxy having from 1 to 39, preferably from 1 to 29, more preferably from 1 to 19, even more preferably from 1 to 9 and most preferably from 1 to 4 carbon atoms,
(iv) —(CH$_2$)$_d$—R$^9$, wherein d is an integer of from 1 to 5 and R$^9$ is selected from the group consisting of
  (a) —SiR$^O$R$^{OO}$R$^{OOO}$, —C≡C—SiR$^O$R$^{OO}$R$^{OOO}$,
  (b) alkyl having from 1 to 19, preferably from 1 to 15, even more preferably from 1 to 10 and most preferably from 1 to 5 carbon atoms,
  (c) alkyl having from 1 to 19, preferably from 1 to 15, even more preferably from 1 to 10 and most preferably from 1 to 5 carbon atoms, wherein two adjacent carbon atoms are replaced by —CR$^O$=CR$^{OO}$— or —C≡C—,
  (d) alkyl having from 1 to 19, preferably from 1 to 15, even more preferably from 1 to 10 and most preferably from 1 to 5 carbon atoms, wherein one or more, preferably non-adjacent, carbon atoms are replaced by a heteroatom or heteroatom group as defined herein,
  (e) aryl having from 6 to 30, preferably from 6 to 18 carbon ring atoms, and
  (f) heteroaryl having from 5 to 30 ring atoms,
with R$^O$, R$^{OO}$, R$^{OOO}$ and X$^O$ as defined herein, wherein said aryl and heteroaryl may be unsubstituted or substituted with one or more groups R$^S$, and wherein said alkyl may be substituted with one or more groups selected from the group consisting of R$^S$, aryl as defined herein and heteroaryl as defined herein.

The heteroatom or heteroatom groups may be selected from the group consisting of —NR$^O$—, —PR$^O$—, —O—, —S—, —SiR$^O$R$^{OO}$—, —C(O)NR$^O$—, —C(O)—, —C(O)O—, —S(O)—, —S(O)(OR$^O$)—, —O—S(O)—O—, —O—P(OR$^O$)—O— and —O—PH(O)—O— if the heteroatom or heteroatom group is not in terminal position, and from the group consisting of —NR$^O$R$^{OO}$, —PR$^O$R$^{OO}$, —OR$^O$, —SR$^O$, —SiR$^O$R$^{OO}$R$^{OOO}$, —C(O)NR$^O$R$^{OO}$, —C(O)R$^O$, —C(O)R$^O$—OR$^{OO}$, —S(O)R$^O$, —S(O)(OR$^O$)R$^{OO}$, —O—S(O)—OR$^O$, —O—P(OR$^O$)(OR$^{OO}$) and —O—PH(O)—OR$^O$ if the heteroatom or heteroatom group is in terminal position.

Preferred examples of R$^B$ may be selected from the group consisting of alkyl having from 1 to 40, preferably from 1 to 30, more preferably from 1 to 20, even more preferably from 1 to 10 and most preferably from 1 to 5 carbon atoms; alkoxy having from 1 to 39, preferably from 1 to 29, more preferably from 1 to 19, even more preferably from 1 to 9 and most preferably from 1 to 4 carbon atoms; —(CH$_2$)$_d$—R$^9$ with d as defined earlier and R$^9$ being alkyl having from 1 to 19, preferably from 1 to 15, even more preferably from 1 to 10 and most preferably from 1 to 5 carbon atoms, wherein two adjacent carbon atoms are replaced by —C≡C—, and —C≡C—SiR$^O$R$^{OO}$R$^{OOO}$.

R$^O$, R$^{OO}$ and R$^{OOO}$ are at each occurrence independently of each other selected from the group consisting H, F, C$_{1-40}$ organyl or organoheteryl, and substituted C$_{1-40}$ organyl or organoheteryl.

X$^O$ is at each occurrence independently selected from the group consisting of F, Cl, Br and I.

R$^S$ may at each occurrence independently be selected from the group consisting of alkyl having from 1 to 30 or from 1 to 20 or from 1 to 10 or from 1 to 5, carbon atoms, halogenated alkyl having from 1 to 30 or from 1 to 20 or from 1 to 10 or from 1 to 5 carbon atoms, aryl having from 6 to 30 or from 6 to 18 carbon ring atoms, aryl having from 6 to 30 or from 6 to 18 carbon ring atoms substituted with at least one group independently selected from the group consisting of F, Cl, Br, I, alkyl having from 1 to 30 or from 1 to 20 or from 1 to 10 or from 1 to 5 carbon atoms, and halogenated alkyl having from 1 to 30 or from 1 to 20 or from 1 to 10 or from 1 to 5 carbon atoms, heteroaryl having from 1 to 30 ring atoms, heteroaryl having from 1 to 30 ring atoms substituted with at least one group independently selected from the group consisting of F, Cl, Br, I, alkyl having from 1 to 30 or from 1 to 20 or from 1 to 10 or from 1 to 5 carbon atoms, and halogenated alkyl having from 1 to 30 or from 1 to 20 or from 1 to 10 or from 1 to 5 carbon atoms.

Examples of alkyl groups suitable for R$^A$ and R$^B$ may be selected from the group consisting of linear alkyl, branched alkyl with at least 3 carbon atoms and cycloalkyl with at least 4 carbon atoms.

Specific examples of suitable alkyl groups may be selected from the group consisting of methyl, ethyl, n-propyl, iso-propyl, n-butyl, iso-butyl, tert-butyl, pentyl, hexyl, heptyl, octyl, nonyl, decyl, undecyl, dodecyl, tridecyl, tetradecyl and pentadecyl.

Examples of alkyl groups suitable for R$^A$ and R$^B$, wherein two adjacent carbon atoms are replaced by —CR$^O$=CR$^{OO}$— or —C≡C— may be selected from the group consisting of alkenyl with at least 2 carbon atoms, alkynyl with at least 2 carbon atoms, allyl having at least 3 carbon atoms, alkyldienyl having at least 4 carbon atoms, and polyenyl having at least 4 carbon atoms.

An alkenyl group, wherein one or more CH$_2$ groups are replaced by —CR$^O$=CR$^{OO}$— can be straight-chain or branched. It is preferably straight-chain, has 2 to 10 C atoms and accordingly is preferably vinyl, prop-1-enyl, or prop-2-enyl, but-1-enyl, but-2-enyl or but-3-enyl, pent-1-enyl, pent-2-enyl, pent-3-enyl or pent-4-enyl, hex-1-enyl, hex-2-enyl, hex-3-enyl, hex-4-enyl or hex-5-enyl, hept-1-enyl, hept-2-enyl, hept-3-enyl, hept-4-enyl, hept-5-enyl or hept-6-enyl, oct-1-enyl, oct-2-enyl, oct-3-enyl, oct-4-enyl, oct-5-enyl, oct-6-enyl or oct-7-enyl, non-1-enyl, non-2-enyl, non-3-enyl, non-4-enyl, non-5-enyl, non-6-enyl, non-7-enyl or non-8-enyl, dec-1-enyl, dec-2-enyl, dec-3-enyl, dec-4-enyl, dec-5-enyl, dec-6-enyl, dec-7-enyl, dec-8-enyl or dec-9-enyl.

Especially preferred alkenyl groups are C$_2$-C$_7$-1E-alkenyl, C$_4$-C$_7$-3E-alkenyl, C$_5$-C$_7$-4-alkenyl, C$_6$-C$_7$-5-alkenyl and C$_7$-6-alkenyl, in particular C$_2$-C$_7$-1E-alkenyl, C$_4$-C$_7$-3E-alkenyl and C$_5$-C$_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Alkenyl groups having up to 5 C atoms are generally preferred.

Examples of alkyl, wherein one or more, preferably non-adjacent, carbon atoms are replaced by a heteroatom or heteroatom group, may be selected from the group consisting of alkoxy, oxaalkyl, ketone and ester.

Suitable examples of alkoxy or oxaalkyl may be selected from the group consisting of methoxy, ethoxy, propoxy, butoxy, pentoxy, hexoxy, heptoxy, octoxy, nonoxy, decoxy, undecoxy, dodecoxy, tridecoxy and tetradecoxy.

An oxaalkyl group, i.e. where one CH$_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example. oxaalkyl, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

In an alkyl group wherein one $CH_2$ group is replaced by —O— and one by —C(O)—, these radicals are preferably neighboured. Accordingly these radicals together form a carbonyloxy group —C(O)—O— or an oxycarbonyl group —O—C(O)—. Preferably this group is straight-chain and has 2 to 6 C atoms. It is accordingly preferably selected from the group consisting of acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl, and 4-(methoxycarbonyl)-butyl.

An alkyl group wherein two or more $CH_2$ groups are replaced by —O— and/or —C(O)O— can be straight-chain or branched. It is preferably straight-chain and has 3 to 12 C atoms. Accordingly it is preferably selected from the group consisting of bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, and 5,5-bis-(ethoxycarbonyl)-hexyl.

A thioalkyl group, i.e where one $CH_2$ group is replaced by —S—, is preferably straight-chain thiomethyl (—$SCH_3$), 1-thioethyl (—$SCH_2CH_3$), 1-thiopropyl (=—$SCH_2CH_2CH_3$), 1-(thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), wherein preferably the $CH_2$ group adjacent to the $sp^2$ hybridised vinyl carbon atom is replaced.

Especially preferred aryl and heteroaryl groups are phenyl, phenyl wherein one or more CH groups are replaced by N, naphthalene, thiophene, selenophene, thienothiophene, dithienothiophene, fluorene and oxazole, all of which can be unsubstituted, mono- or polysubstituted with $R^S$ as defined herein. Very preferred rings are selected from pyrrole, preferably N-pyrrole, furan, pyridine, preferably 2- or 3-pyridine, pyrimidine, pyridazine, pyrazine, triazole, tetrazole, pyrazole, imidazole, isothiazole, thiazole, thiadiazole, isoxazole, oxazole, oxadiazole, thiophene, preferably 2-thiophene, selenophene, preferably 2-selenophene, thieno[3,2-b]thiophene, thieno[2,3-b]thiophene, furo[3,2-b]furan, furo[2,3-b]furan, seleno[3,2-b]selenophene, seleno[2,3-b]selenophene, thieno[3,2-b]selenophene, thieno[3,2-b]furan, indole, isoindole, benzo[b]furan, benzo[b]thiophene, benzo[1,2-b;4,5-b']dithiophene, benzo[2,1-b;3,4-b']dithiophene, quinole, 2-methylquinole, isoquinole, quinoxaline, quinazoline, benzotriazole, benzimidazole, benzothiazole, benzisothiazole, benzisoxazole, benzoxadiazole, benzoxazole, benzothiadiazole, all of which can be unsubstituted, mono- or polysubstituted with $R^S$ as defined herein.

Exemplary organic binders may be selected from the group consisting of the following formulae (I-1) to (I-16)

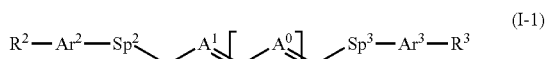
(I-1)

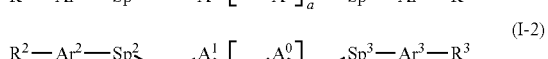
(I-2)

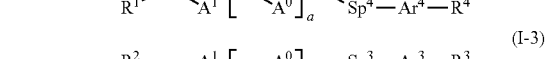
(I-3)

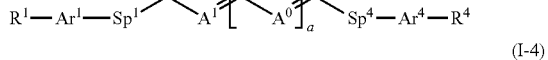
(I-4)

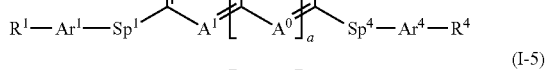
(I-5)

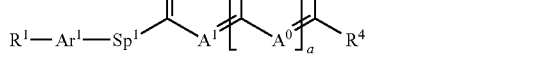
(I-6)

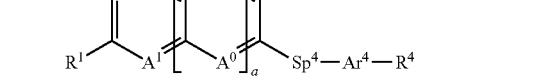
(I-7)

(I-8)

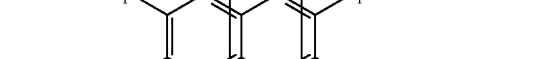
(I-9)

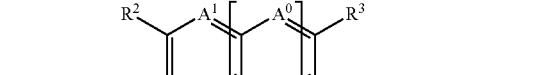
(I-10)

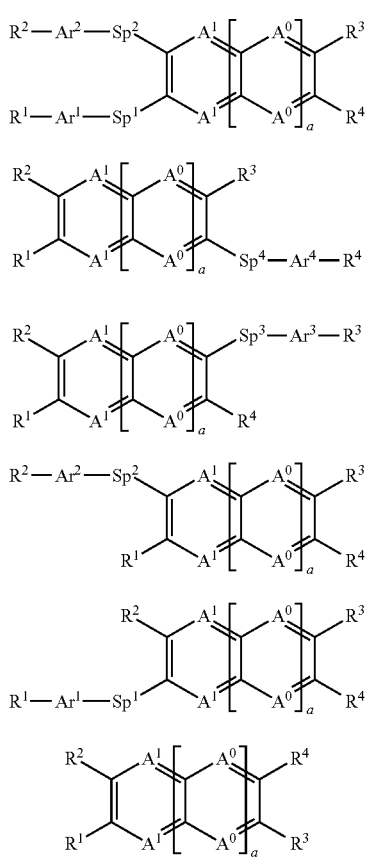

(I-11)
(I-12)
(I-13)
(I-14)
(I-15)
(I-16)

with $A^0$, $A^1$, $Ar^1$, $Ar^2$, $Ar^3$, $Ar^4$, $Sp^1$, $Sp^2$, $Sp^3$, $Sp^4$, $R^1$, $R^2$, $R^3$, $R^4$, a, b1, b2, b3, b4, c1, c2, c3 and c4 as defined herein.

Preferred examples of organic binders may be selected from the group consisting of formulae (I-7), (I-10), (I-12), (I-13), (I-14), (I-15) and (I-16). More preferred examples of organic binders may be selected from the group consisting of formulae (I-12), (I-13), (I-14), (I-15) and (I-16). The most preferred example is formula (I-16).

It is noted that in any of formulae (I-1) to (I-16) the central unit of formula (II) may be any one selected from the group consisting of formulae (II-a) to (II-e).

With respect to any one of formulae (I-a) to (I-q) it is preferred that the $A^0$ adjacent to $R^3$ is N or the $A^0$ adjacent to $R^4$ is N or—more advantageously—both are N.

Examples of the organic binder of formula (I-16) may be selected from the group consisting of the following formulae (I-16-a) to (I-16-e)

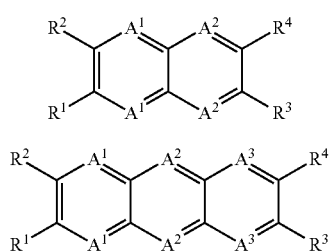

(I-16-a)
(I-16-b)

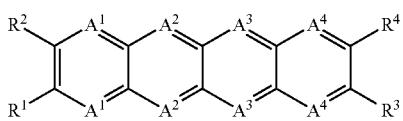

(I-16-c)

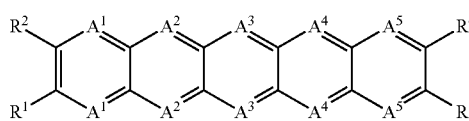

(I-16-d)

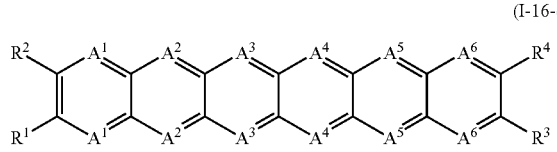

(I-16-e)

wherein $A^1$, $A^2$, $A^3$, $A^4$, $A^5$, $A^6$, $R^1$, $R^2$, $R^3$ and $R^4$ are as defined herein.

Specific examples of the organic binder may be selected from the group consisting of the following formulae (V-a) to (V-h)

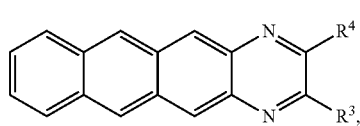

(V-a)

wherein $R^3$ and $R^4$ are as defined above, and are preferably identical and/or are preferably selected from the group consisting of $CH_3$, $CH_2Br$, Ph, Ph-Br, Ph-F, Ph-$OCH_3$, Ph-OH, Ph-O—$(CH_2)_3$—P(O)(OH)$_2$

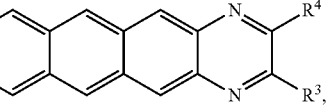

(V-b)

wherein $R^3$ and $R^4$ are as defined above, and are preferably identical and/or are preferably selected from the group consisting of $CH_3$, $CH_2Br$, Ph, Ph-F and Ph-$CF_3$

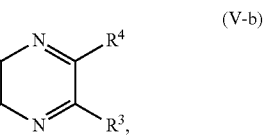

(V-c)

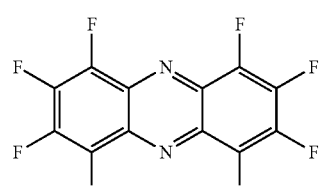

(V-d)

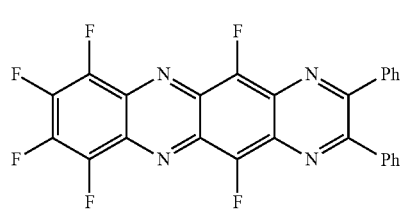

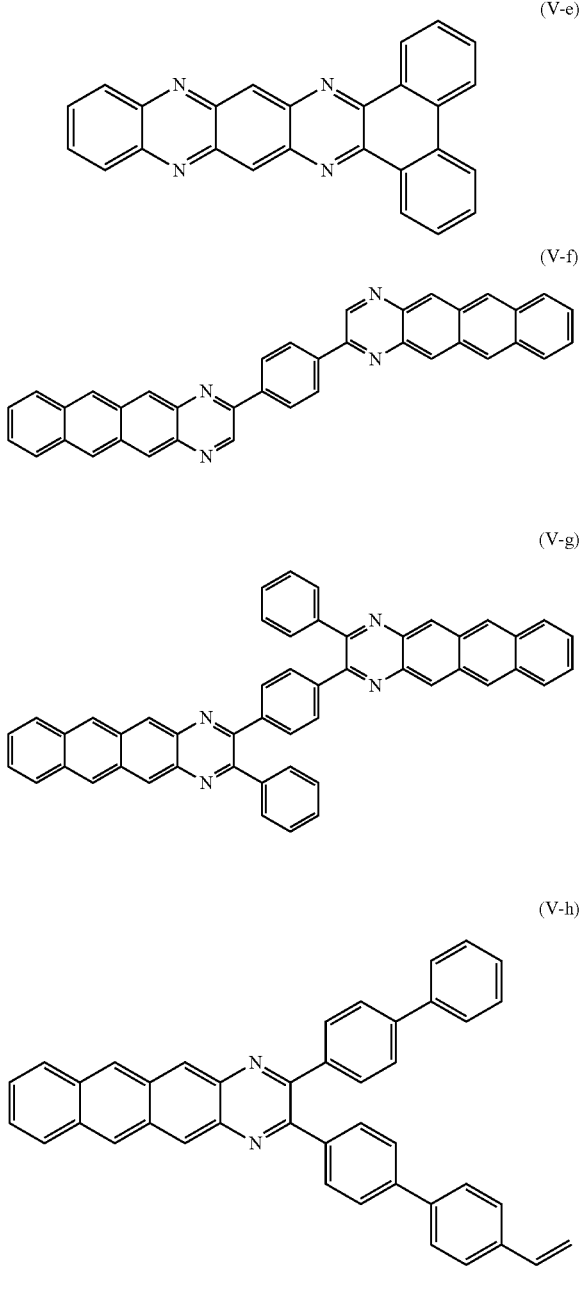

(V-e)

(V-f)

(V-g)

(V-h)

One of the advantages of the present organic binder, as will further be illustrated in the following as well as in the examples, is that it can easily be modified in order to match the molecular orbital levels to those of the inorganic semiconducting material also comprised in the semiconductor composition of the present application. The organic binders of the present application offer surprising versatility in terms of potential substituents suitable for fine-tuning the molecular orbital energies, particularly those of the highest occupied molecular orbital (HOMO) and the lowest unoccupied molecular orbital (LUMO), all the while remaining easy to synthesize as will be shown in the following. Furthermore, the present organic binder also offers sufficient flexibility to additionally introduce substituents that may aid in improving its solubility in various solvents that are commonly used in the preparation of organic electronic devices.

The organic binders of the present application have proven particularly useful in combination with an inorganic semiconducting material. The present organic binders have surprisingly proven to drastically improve charge mobility in inorganic semiconducting materials, particularly in n-type semiconducting materials, without having to revert to a thermal post-treatment, thereby permitting the use of flexible organic substrates in organic electronic devices.

Synthesis of the Organic Binder

The present organic binders can be synthesized using chemical reactions well known to the skilled person as is illustrated in the following and in more detail in the examples included in the present application.

For example, Scheme 1 shows the synthesis of 2,3-disubstituted naphtho[2,3-g]quinoxaline starting from 2-aminoanthraquinone. In a first reaction sequence comprising the first four reaction steps shown in Scheme 1, the 2-aminoanthraquinone is converted to 2,3-diaminoanthraquinone in accordance with the method published by A. Schaarschmidt and H. Leu in Justus Liebigs Annalen der Chemie 1915, 407, 176-194. The 2,3-diaminoanthraquinone is then reduced with zinc powder activated with copper(II) sulfate. In comparison to the published synthetic procedure (M. Clark, Journal of the Chemical Society C, 1966, 277-283; E. Leete, O. Ekechukwu, P. Delvigs, Journal of Organic Chemistry, 1966, 3743-3739) the use of activated zinc powder leads to essentially complete conversion of the 2,3-diaminoanthraquinone, thereby allowing for simplified and more efficient purification by re-crystallization instead of column chromatography. The so-obtained pure 2,3-diaminoanthraquinone is then reacted with the respective di-ketone resulting in formation of the desired 2,3-disubstituted naphtho[2,3-g]quinoxaline, which may then be further purified for example by re-crystallization from a suitable solvent.

Scheme 1 - Synthesis of 2,3-disubstituted naphtho[2,3-g]quinoxaline

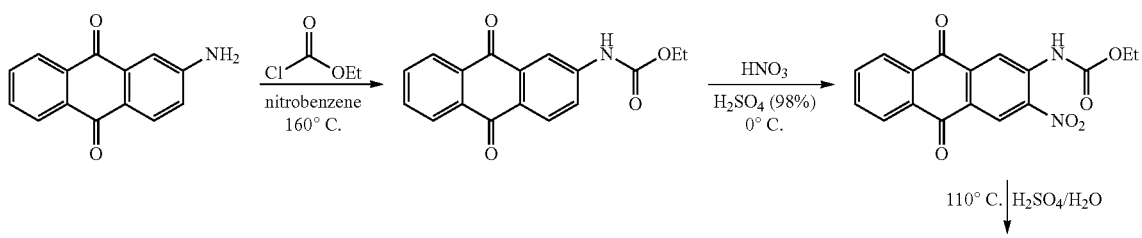

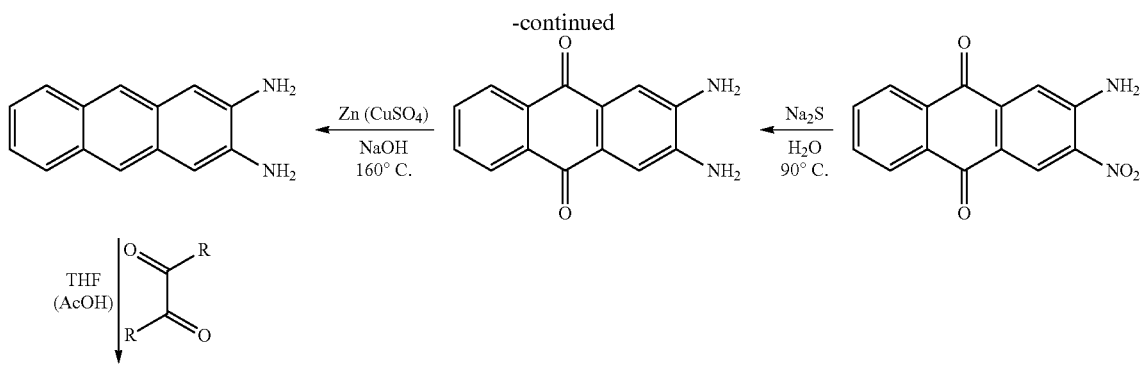

The synthesis of 2,3-disubstituted pyrazino[2,3-b] phenazine may for example be performed as in analogy to A. M. Amer et al., Monatshefte für Chemie, 1999, 1217-1225 by reacting 2,3-diaminophenyzine with the respective diketone to obtain the desired 2,3-disubstituted pyrazino[2,3-b]phenazine as is shown in Scheme 2. It was found that in comparison to the published reaction conditions higher purity can be obtained by modifying reaction conditions and performing the reaction in tetrahydrofuran (THF) or methanol as solvent instead of in boiling acetic acid and only adding 2 ml of glacial acetic acid per 55 ml of solvent, thus allowing the so-obtained product to have sufficient purity following filtration and washing to be use in any subsequent step. If necessary the 2,3-disubstituted pyrazino[2,3-b] phenazine can be further purified by sublimation.

Scheme 2 - Synthesis of 2,3-disubstituted pyrazino[2,3-b]phenazine

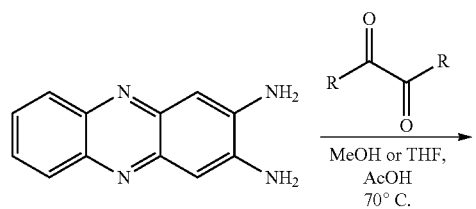

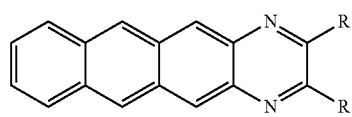

The synthesis of fluorinated pyrazino[2,3-b]phenazines is illustrated using 5,7,8,9,10,12-hexafluoro-2,3-diphenylpyrazino[2,3-b]phenazine as example. The preferred synthetic route is illustrated in Scheme 3 and includes a total of 6 steps, wherein the pyrazino[2,3-b]phenazine is assembled from octafluorophenazine and 1,2-diphenylethane-1,2-diamine. Octafluorophenazine may be obtained in a single reaction step starting from the commercially available pentafluoroaniline. 1,2-diphenylethane-1,2-diamine may be obtained in a three-step synthesis starting with the commercially available meso-hydrobenzoin, first tosylating the hydroxy groups of the hydrobenzoin, then reacting the so-obtained intermediate product with sodium azide (NaN₃) to yield diphenylethane-1,2-diazide and finally reducing said diazide with LiAlH₄ to 1,2-diphenylethane-1,2-diamine. In the following octafluorophenazine and 1,2-diphenylethane-1,2-diamine are reacted with triethylamine in dimethylformamide as solvent to yield 5,7,8,9,10,12-hexafluoro-2,3-diphenyl-1,2,3,4-tetrahydropyrazino[2,3-b]phenazine, which may then be oxidized with 1,2-dichloro-5,6-dicyano-1,4-benzoquinone to yield 5,7,8,9,10,12-hexafluoro-2,3-diphenylpyrazino[2,3-b]phenazine. The so-obtained crude product may be purified by washing with hot tetrahydrofuran and subsequent sublimation.

Scheme 3 - Synthesis of 5,7,8,9,10,12-hexafluoro-2,3-diphenylpyrazino[2,3-b]phenazine

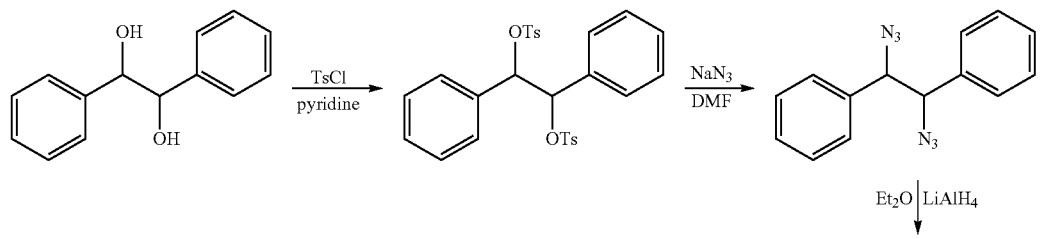

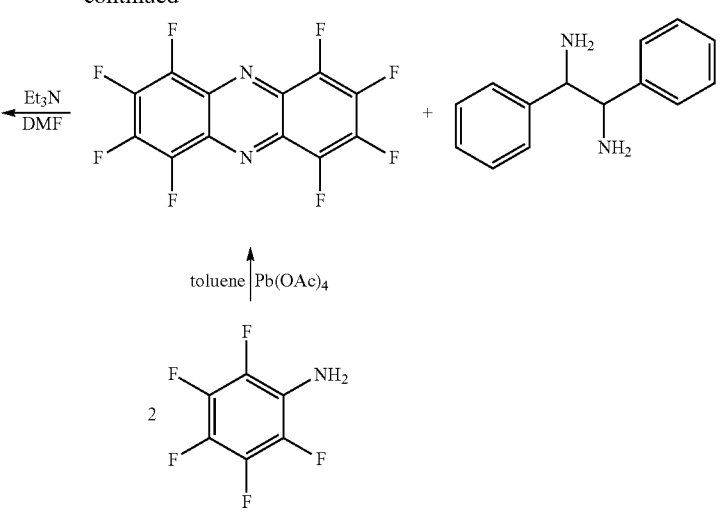

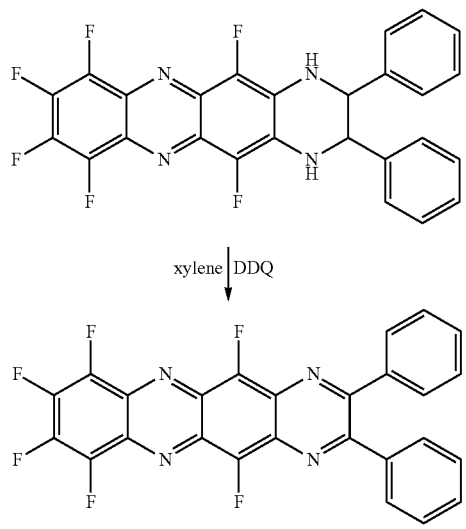

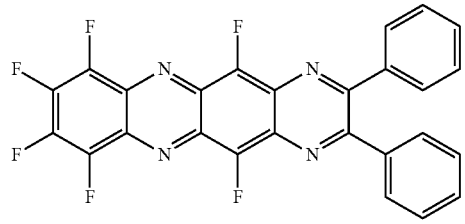

Formulation

Another aspect of the present application relates to a formulation comprising the inorganic binder of the present application and one or more solvent. Preferred solvents are organic solvents.

Preferred examples of such solvents may be selected from the group consisting of water, aliphatic hydrocarbons, chlorinated hydrocarbons, aromatic hydrocarbons, ketones, ethers and mixtures thereof. More preferred examples are selected from the group consisting of alcohols, ethers, haloalkanes and any mixture of these.

Suitable examples of alcohols, ethers and haloalkanes may be selected as disclosed in respect to the dispersant.

Exemplary solvents which may be used include 1,2,4-trimethylbenzene, 1,2,3,4-tetra-methyl benzene, pentylbenzene, mesitylene, cumene, cymene, cyclohexylbenzene, diethylbenzene, tetralin, decalin, 2,6-lutidine, 2-fluoro-m-xylene, 3-fluoro-o-xylene, 2-chlorobenzotrifluoride, N,N-dimethylformamide, 2-chloro-6-fluorotoluene, 2-fluoroanisole, anisole, 2,3-dimethylpyrazine, 4-fluoroanisole, 3-fluoroanisole, 3-trifluoro-methylanisole, 2-methylanisole, phenetol, 4-methylanisole, 3-methylanisole, 4-fluoro-3-methylanisole, 2-fluorobenzonitrile, 4-fluoroveratrol, 2,6-dimethylanisole, 3-fluorobenzo-nitrile, 2,5-dimethylanisole, 2,4-dimethylanisole, benzonitrile, 3,5-dimethyl-anisole, N,N-dimethylaniline, ethyl benzoate, 1-fluoro-3,5-dimethoxy-benzene, 1-methylnaphthalene, N-methylpyrrolidinone, 3-fluorobenzo-trifluoride, benzotrifluoride, dioxane, trifluoromethoxy-benzene, 4-fluorobenzotrifluoride, 3-fluoropyridine, toluene, 2-fluoro-toluene, 2-fluorobenzotrifluoride, 3-fluorotoluene, 4-isopropylbiphenyl, phenyl ether, pyridine, 4-fluorotoluene, 2,5-difluorotoluene, 1-chloro-2,4-difluorobenzene, 2-fluoropyridine, 3-chlorofluoro-benzene, 1-chloro-2,5-difluorobenzene, 4-chlorofluorobenzene, chloro-benzene, o-dichlorobenzene, 2-chlorofluorobenzene, p-xylene, m-xylene, o-xylene or mixture of o-, m-, and p-isomers. Examples of especially preferred solvents include, without limitation, dichloromethane, trichloromethane, chlorobenzene, o-dichlorobenzene, tetrahydrofuran, anisole, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, N,N-dimethylformamide, dimethylacetamide, dimethylsulfoxide, tetraline, decaline, indane, methyl benzoate, ethyl benzoate, mesitylene and/or mixtures thereof.

Preferred organic solvents are chlorinated hydrocarbons, of which dichloromethane ($CH_2Cl_2$) is most preferred.

Devices

The present semiconductor composition may be used in electronic devices, for example in organic electronic devices, as semiconducting layer, preferably as n-type semiconducting layer. Thus, the present application also provides for an organic electronic device comprising the present semiconductor composition. Preferably the present semiconductor composition is comprised in the organic electronic device in form of a semiconducting layer. Thus, the present application preferably provides for an organic electronic device comprising a semiconducting layer consisting of the present semiconductor composition.

Examples of such organic electronic devices may be selected from the group consisting of optical, electrooptical, electronic, electroluminescent or photoluminescent components or devices. Preferred examples may be selected from the group consisting of organic field effect transistors (OFET), thin film transistors (TFT), integrated circuits (IC), logic circuits, capacitors, radio frequency identification (RFID) tags, devices or components, organic light emitting diodes (OLED), organic light emitting transistors (OLET), flat panel displays, backlights of displays, organic photovoltaic devices (OPV), organic solar cells (O-SC), photodiodes, laser diodes, photoconductors, organic photodetectors (OPD), electrophotographic devices, organic memory devices, sensor devices, charge injection layers, charge transport layers or interlayers in polymer light emitting diodes (PLEDs), Schottky diodes, planarising layers, antistatic films, conducting substrates, conducting patterns, electrode materials in batteries, alignment layers, biosensors, biochips, security markings, security devices, and components or devices for detecting and discriminating DNA sequences. Of these, in turn, organic field effect transistors (OFET), thin film transistors (TFT), integrated circuitry (IC), radio frequency identification (RFID) tags, organic light emitting devices (OLED), organic light emitting transistors (OLET) and backlights of displays are preferred.

It is preferred that the present organic electronic devices comprise an anode, a cathode and a functional layer. Said functional layer may in the case of organic light emitting diodes (OLEDs) for example be a light-emitting layer, or in the case of an organic photovoltaic cell a photoactive layer, or in case of an organic field effect transistor or a thin film transistor a semiconducting layer.

Preferably the present organic electronic device further comprise at least one layer selected from the group consisting of electron transport layer, hole transport layer, hole injection layer, electron injection layer, exciton blocking layer, interlayers and charge generation layers.

A preferred sequence of layers for an OLED may be as follows:
  anode,
  optional hole injection layer,
  optional one or more hole transport layer,
  light emitting layer,
  optional electron transport layer,
  optional electron injection layer, and
  cathode.

It is noted that any layer indicated as "optional" may either be present or absent.

The anode is generally formed of an electrically conductive material. Exemplary electrically conductive materials include electrically conductive metals, electrically conductive alloys, electrically conductive polymers, and electrically conductive metal oxides. Exemplary electrically conductive metals include gold, silver, copper, aluminum, nickel, palladium, platinum, and titanium. Exemplary electrically conductive alloys include stainless steel (e.g., 332 stainless steel, 316 stainless steel), alloys of gold, alloys of silver, alloys of copper, alloys of aluminum, alloys of nickel, alloys of palladium, alloys of platinum, and alloys of titanium. Exemplary electrically conducting polymers include polythiophenes (e.g., doped poly(3,4-ethylenedioxythiophene)), polyanilines (e.g., doped polyanilines), polypyrroles (e.g., doped polypyrroles). Exemplary electrically conducting metal oxides include indium tin oxide, indium zinc oxide, fluorinated tin oxide, tin oxide and zinc oxide.

It is preferred that the anode is formed of a material with high work function, for example with a work function of at least 4.5 eV versus vacuum. In some embodiments, blends or combinations of electrically conductive materials are used. In some embodiment, it may be advantageous to form the anode of transparent material, such as for example indium tin oxide or indium zinc oxide. Alternatively the anode may comprise more than one layer, for example it may comprise an inner layer of indium tin oxide and an outer layer of tungsten oxide, molybdenum oxide or vanadium oxide.

The cathode is generally formed of an electrically conductive material, preferably one with a low work function. Exemplary materials suitable are metals such as earth alkaline metals, main group metals or lanthanide. Particular examples of such metals are Ca, Ba, Mg, Al, In, Yb, Sm and Eu as well as alloys thereof. It is also possible to use alloys of silver and an alkaline or alkaline earth metal, such as for example an alloy of silver and magnesium. The cathode may also be formed of more than one layer, in which case metals or alloys having a higher work function may be present. Examples of such metals or alloys having a higher work function are Ag, Al, Ca/Ag alloy, Mg/Ag alloy and Ba/Ag alloy.

In some embodiments the cathode may also comprise a layer of material having a high dielectric constant. Examples of suitable materials are metal fluorides, oxides or carbonates with the metal selected from the alkaline and alkaline earth metals. Specific examples of such materials are LiF, $Li_2O$, $BaF_2$, MgO, NaF, CsF, $Cs_2CO_3$ or $CaF_2$. Lithium chinolate may also be used.

As suitable material for a charge transport layer, particularly for a hole transporting layer, the present semiconducting composition may be used.

A first preferred OPV device according to the invention comprises the following layers (in the sequence from bottom to top):
  optionally a substrate,
  a high work function electrode, preferably comprising a metal oxide, like for example ITO, serving as anode,
  an optional conducting polymer layer or hole transport layer, preferably comprising an organic polymer or polymer blend, for example of PEDOT:PSS (poly(3,4-ethylenedioxythiophene):poly(styrene-sulfonate), or TBD (N,N'-dyphenyl-N—N'-bis(3-methylphenyl)-1,1'biphenyl-4,4'-diamine) or NBD (N,N'-dyphenyl-N—N'-bis(1-napthylphenyl)-1,1'biphenyl-4,4'-diamine),
  a layer, also referred to as "active layer", comprising a p-type and an n-type organic semiconductor, which can exist for example as a p-type/n-type bilayer or as distinct p-type and n-type layers, or as blend or p-type and n-type semiconductor, forming a bulk heterojunction (BHJ),
  optionally a layer having electron transport properties, for example comprising LiF,
  a low work function electrode, preferably comprising a metal like for example aluminum, serving as cathode,
  wherein at least one of the electrodes, preferably the anode, is transparent to visible light, and wherein the present semiconductor composition may for example be used in the photoactive layer.

A second preferred OPV device according to the invention is an inverted OPV device and comprises the following layers (in the sequence from bottom to top):
  optionally a substrate,
  a high work function metal or metal oxide electrode, comprising for example ITO, serving as cathode,
  a layer having hole blocking properties, preferably comprising a metal oxide like $TiO_x$ or $Zn_x$,
  an active layer comprising a p-type and an n-type organic semiconductor, situated between the electrodes, which can exist for example as a p-type/n-type bilayer or as distinct p-type and n-type layers, or as blend or p-type and n-type semiconductor, forming a bulk heterojunction (BHJ),
  an optional conducting polymer layer or hole transport layer, preferably comprising an organic polymer or polymer blend, for example of PEDOT:PSS or TBD or NBD,
  an electrode comprising a high work function metal like for example silver, serving as anode,
  wherein at least one of the electrodes, preferably the cathode, is transparent to visible light, and wherein the present semiconductor composition may for example be used in the photoactive layer.

The present semiconductor composition may also be suitable for use in an OFET or TFT for example as channel material. Accordingly, the present application also provides and OFET comprising a gate electrode, an insulting (or gate insulator) layer, a source electrode, a drain electrode and a channel connecting the source and drain electrodes, wherein said channel comprises the semiconductor composition of the present application. Other features of an OFET are well known to those skilled in the art and need not be described in more detail.

OFETs where an OSC material is arranged as a thin film between a gate dielectric and a drain and a source electrode, are generally known, and are described for example in U.S. Pat. Nos. 5,892,244, 5,998,804, 6,723,394 and in the references cited in the background section. Due to the advantages, like low cost production using the solubility properties of the compounds according to the invention and thus the processability of large surfaces, preferred applications of these FETs are such as integrated circuitry, TFT displays and security applications.

The gate, source and drain electrodes and the insulating and semiconducting layer in the OFET device may be arranged in any sequence, provided that the source and drain electrodes are separated from the gate electrode by the insulating layer, the gate electrode and the semiconducting layer both contact the insulating layer, and the source electrode and the drain electrode both contact the semiconducting layer.

An OFET device according to the present invention preferably comprises:
  a source electrode,
  a drain electrode,
  a gate electrode,
  a semiconducting layer,
  one or more gate insulator layers, and
  optionally a substrate,
wherein the semiconducting layer preferably comprises the semiconductor composition of the present application.

The OFET device can be a top gate device or a bottom gate device. Suitable structures and manufacturing methods of an OFET device are known to the skilled in the art and are described in the literature, for example in US 2007/0102696 A1.

The present semiconductor composition is useful in the production of organic electronic devices. In particular, the present semiconductor composition is useful for the production of a semiconducting layer comprised in an organic electronic device. Preferably said semiconducting layer is an n-type semiconducting layer.

Hence, the present application also discloses a process for the production of an organic electronic device, said process comprising the steps of
  (A-i) providing a dispersion of an inorganic semiconducting nanoparticle material as defined herein in a dispersant as defined herein;
  (A-ii) applying said dispersion to a substrate;
  (A-iii) removing said dispersant, thus obtaining a layer of an inorganic semiconducting nanoparticles material;
  (A-iv) providing a solution of an organic binder as defined herein in a solvent as defined herein;
  (A-v) applying said solution to the layer of an inorganic semiconducting nanoparticle material obtained in step (A-iii); and
  (A-vi) removing said solvent,
to obtain a semiconducting layer consisting of the present semiconductor composition.

It is noted that, optionally, steps (A-iv) and (A-v) may be repeated in sequence a number of times so as to achieve complete impregnation of the layer of inorganic semiconducting nanoparticles material. Said steps (A-iv) and (A-v) may for example be repeated 2, 3, 4, 5, 6, 7, 8, 9 or 10 times.

Alternatively, the present application discloses a process for the production of an organic electronic device, said process comprising the steps of (B-i) mixing an inorganic semiconducting nanoparticles material as defined herein, an organic binder as defined herein and a solvent to obtain a semiconductor formulation;
  (B-ii) applying said semiconductor formulation to a substrate; and
  (B-iii) removing said solvent,
to obtain a semiconducting layer consisting of the present semiconductor composition.

The application of the dispersion in step (A-ii), the solution in step (A-iii) or the formulation in step (B-ii) may generally be done with any suitable liquid deposition technique. Preferred deposition techniques may be selected from the group consisting of dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, curtain coating, brush coating, slot dye coating or pad printing. Of these, ink jet printing is particularly suitable for use in the present processes.

Ink jet printing is particularly preferred when high resolution layers and devices need to be prepared. Selected formulations of the present invention may be applied to prefabricated device substrates by ink jet printing or microdispensing. Preferably industrial piezoelectric print heads such as but not limited to those supplied by Aprion, Hitachi-Koki, InkJet Technology, On Target Technology, Picojet, Spectra, Trident, Xaar may be used to apply the organic semiconducting layer to a substrate. Additionally semi-industrial heads such as those manufactured by Brother, Epson, Konica, Seiko Instruments Toshiba TEC or single nozzle microdispensers such as those produced by Microdrop and Microfab may be used.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

Test Methods

The used reagents and solvents were purchased from commercial suppliers and were used without further purification. Dry THF was prepared by distillation from sodium/benzophenone under nitrogen atmosphere. The silica gel used for column chromatography possessed a particle size of 40-63 µm. 4,4'bis(trifluoromethyl)benzil was synthesized according to the literature procedure (H. Wang, Y. Wen, X. Yang, Y. Wang, W. Zhou, S. Zhang, X. Zhan, Y. Liu, Z. Shuai, D. Zhu, *Applied Materials and Interfaces*, 2009, 1, 1122-1129.).

$^1$H- and $^{13}$C-NMR spectra were recorded on a 300 (Avance II, Avance III) or 500 (DRX500) MHz spectrometer from Bruker. Chemical shifts (δ) are listed in parts per million (ppm). The $^1$H values are referenced on the TMS signal. The $^{13}$C values are reported relative to the solvent residual peaks of $CDCl_3$, $CD_2Cl_2$, DMSO-$d_6$ and THF-$d_8$ present in the deuterated solvents (H. E. Gottlieb, V. Kotlyar, A. Nudelman, *J. Org. Chem.*, 1997, 62, 7512-7515.).

MS spectra were recorded on a Finnigan MAT 95 spectrometer and EI ionization was used.

Cyclic voltammetry measurements were performed in 0.1 mol/l tetrabutylammonium hexafluorophosphate (TBAPF$_6$) solution in dry THF using a glassy carbon working electrode, a platinum wire as counter electrode and a silver wire as quasi reference electrode. The measurement was carried out under nitrogen atmosphere with a VMP2 from Princeton Applied Research at a potential scan rate of 20 mV/s. The compounds were measured in solution. Ferrocene was added as internal standard in a second measurement. The cyclic voltammograms were calibrated by the formal potential of ferrocene which is 0.4 V versus SCE (C. M. Cardona, W. Li, A. E. Kaifer, D. Stockdale, G. C. Bazan, *Advanced Materials* 2011, 23, 2367-2371.). Using the equation from Leeuw et al. (D. M. de Leeuw, M. M. J. Simenon, A. R. Brown, R. E. F. Einerhand, Synth. Met., 1997, 87, 53.) ($E_{LUMO}=-(E_{onset,red}+4.4)$ and $E_{HOMO}=-(E_{onset,ox}+4.4)$) the HOMO- and LUMO-energies were calculated from the onset potentials of the first reduction and the oxidation wave (vs SCE). Furthermore the difference of the onset potentials was used to calculate the HOMO-LUMO gap ($E_{gap,cv}=E_{onset,ox}-E_{onset,red}$) (Y. Li, Y. Cao, J. Gao, D. Wang, G. Yu, A. J. Heeger, *Synth. Met.*, 1999, 99, 243-248.).

If no oxidation could be observed in the cyclic voltammogram, the HOMO-energy was calculated from the LUMO-energy and the optical band gap predicted from the UV-VIS measurements $E_{HOMO}*=E_{LUMO}-\Delta E_{gap,opt}$.

UV-VIS spectra were recorded in 0.01 mmol/l solutions of the compounds in THF with a TIDAS II from J&M Analytische Meß-und Regeltechnik.

TGA measurements were performed with a TG 209 F1 Iris from Netzsch. The temperature was raised from 30° C. to 600° C. in steps of 10 K/min.

EXAMPLES

The following examples are to illustrate the advantages of the present invention in a non-limiting way.

Example 1—Synthesis of Anthraquinone-2-urethane

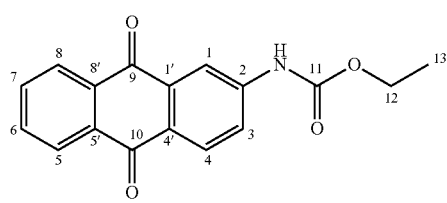 [SMILES: CCOC(=O)Nc1ccc2c(c1)C(=O)c1ccccc1C2=O]

In a 500 ml three-necked flask 13.2 ml (111 mmol, 1.7 eq.) ethylchloroformate were added to a mixture of 17.92 g (80 mmol, 1 eq.) 2-amino-anthraquinone in 170 ml nitrobenzene. The resulting brown mixture was heated to 160° C. for 45 min and then cooled to room temperature, accompanied by the formation of a precipitate, which was collected by filtration, washed with acetone and subsequently dried in a rotary evaporator to yield 20.16 g (69 mmol, 86%) anthraquinone-2-urethane.

EI-MS: m/z=295 (M$^+$)

Example 2—Synthesis of 3-nitro-anthraquinone-2-urethane

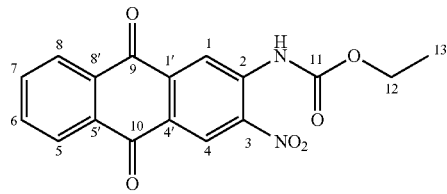 [SMILES: CCOC(=O)Nc1cc2c(cc1[N+](=O)[O-])C(=O)c1ccccc1C2=O]

In a 250 ml three-necked flask equipped with reflux condenser and dropping funnel 10 g (34 mmol, 1.0 eq.) anthraquinone-2-urethane were dissolved in 50 ml sulfuric acid (98%). The resulting deep-red solution was cooled to 0° C. in an ice-bath. Subsequently a mixture of 2.5 ml nitric acid (conc.) and 25 ml of sulfuric acid (98%) was slowly added to the deep-red solution by means of the dropping funnel. After stirring at 0° C. for two hours the mixture was poured into 600 ml ice water, resulting in the precipitation of a yellow solid, which was collected by filtration and dried in a rotary evaporator. The solid is re-crystallized from nitrobenzene. 5.68 g (17 mmol, 49%) 3-nitro-anthraquinone-2-urethane could be obtained.

$^1$H-NMR (500 MHz, C$_6$D$_6$, 300 K): δ=0.937 (t, CH$_3$, 13-H$_3$), 3.925 (q, CH$_2$, 12-H$_2$) 7.054 (m, CH, 5/8-H$_2$), 8.120-8.182 (m, CH, 6/7-H$_2$), 8.911 (s, 4-H), 9.608 (s, CH, 1-H), 9.764 (s, NH, H$_1$) ppm.

$^{13}$C-NMR (125 MHz, CDCl$_3$, 300 K): δ=14.77 (13-C), 63.00 (12-C), 119.92 (1-C), 126.76 (4-C), 127.61 (3-C), 127.90/128.11 (6/7-C), 134.35/134.44 (5'/8'-C), 134.66/134.92 (5/8-C), 138.21 (2-C), 138.73 (4'-C), 139.92 (1'-C), 152.97 (11-C), 180.53 (10-C), 181.67 (9-C) ppm.

Example 3—Synthesis of 2-amino-3-nitro-anthraquinone

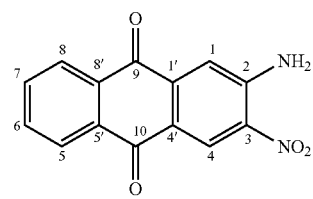 [SMILES: Nc1cc2c(cc1[N+](=O)[O-])C(=O)c1ccccc1C2=O]

In a 100 ml two-necked flask with reflux condenser 4.498 g (13 mmol, 1 eq.) 3-nitro-anthraquinone-2-urethane were dissolved in 4 ml distilled water and 23 ml sulfuric acid (conc.). The red solution was heated to 110° C. for one hour, subsequently allowed to cool and poured into 100 ml of ice-cold distilled water, resulting in a yellow solid, which was collected and dried. The product could be used in the following step without further purification.

Example 4—Synthesis of 2,3-diamino-anthraquinone

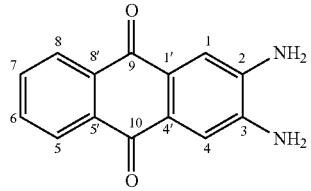 [SMILES: Nc1cc2c(cc1N)C(=O)c1ccccc1C2=O]

To a suspension of the total amount of the 2-amino-3-nitro-anthraquinone produced in Example 3 in 25 ml distilled water were slowly added 10.65 g Na$_2$S·9 H$_2$O (44 mmol, 4.4 eq.). In the beginning strong foaming was observed. Subsequently the mixture was heated to 90° C. for one hour, resulting in the precipitation of a dark-red solid, which was collected by filtration, washed with distilled water and dried in a rotary evaporator. 2.39 g (0.01 mol, 77% total yield over Examples 3 and 4) 2,3-diamino-amthraquinone were obtained.

$^1$H-NMR (500 MHz, THF-d$_8$, 300 K): δ=5.128 (NH$_2$, H$_4$), 7.417 (s, CH, 1/4-H$_2$), 7.722 (m, CH, 6/7-H$_2$), 8.187 (m, CH, 5/8-H$_2$) ppm.

$^{13}$C-NMR (125 MHz, THF-d$_8$, 300 K): δ=112.81 (1/4-C), 127.80 (5/8-C) 127.91 (1'/4'-C), 134.28 (6/7-C), 136.17 (5'/8'-C), 142.36 (2/3-C), 183.19 (9/10-C) ppm.

Example 5—Synthesis of 2,3-diaminoanthracene

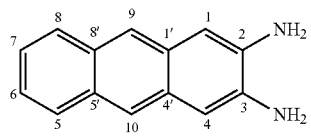

57.3 g zinc powder and a solution of 0.1 g CuSO$_4$·5 H$_2$O in 3.5 ml distilled water were stirred for 15 min in a 1l three neck flask equipped with a reflux condenser, followed by the subsequent addition of 20.39 g (86 mmol, 1 eq.) 2,3-diamino-anthraquinone and 285 ml aqueous NaOH (5%). The mixture was heated to 140° C., accompanied by heavy foaming and the precipitation of a yellow solid, then stirred for 16 hours in an oil bath having a temperature of 160° C. and filtered hot. The resulting solid was dried, stirred in THF and filtered. The filtrate is freed of solvent in a rotary evaporator, and the obtained solid re-crystallized from nitrobenzene, yielding 4.00 g (19 mmol, 22%) 2,3-diamino-anthracene, which was subsequently purified by extraction of the solid with hot toluene. The 2,3-diaminoanthrcene precipitated from the toluene solution as gold-colored platelets with a purity of over 98% (by weight).

$^1$H-NMR (500 MHz, THF d$_8$, 300 K): δ=4.608 (NH$_2$, H$_4$), 7.047 (s, CH, 1/4-H$_2$), 7.224 (m, CH, 6/7-H$_2$), 7.802 (m, CH, 5/8-H$_2$), 7.963 (s, CH, 9/10-H$_2$) ppm.

$^{13}$C-NMR (75 MHz, THF d$_8$, 300 K): δ=108.24 (1/4-C), 123.15 (9/10-C) 124.47 (6/7-C), 129.02 (6/8-C), 131.58 (1'/4'-C), 131.91 (5'/8'-C), 140.63 (2/3-C) ppm.

EI-MS: m/z=208 (M$^+$)

Example 6—Synthesis of 2,3-dimethylnaphtho[2,3-g]quinoxaline

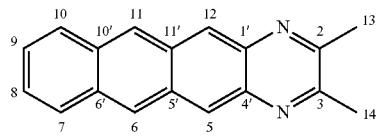 [SMILES: Cc1nc2cc3cc4ccccc4cc3cc2nc1C]

To 2.508 g (12 mmol, 1 eq.) 2,3-diaminoanthracene suspended in 90 ml dry THF and heated to 65° C. in a 250 ml two neck flask 10.75 ml (123 mmol, 10 eq.) 2,3-butanedione (H$_3$C—C(=O)—C(=O)—CH$_3$) were added. After 20 min the reaction mixture is cooled in the dark and then filtered. The orange-red residue was then re-crystallized from toluene. 2.163 g (8 mmol, 69%) 2,3-dimethylnaphtho[2,3-g]quinoxaline were obtained.

$^1$H-NMR (500 MHz, THF-d$_8$, 300 K): δ=2.784 (s, CH$_3$, 13/14-H$_6$), 7.481 (m, CH$_{arom}$, 8/9-H$_2$), 8.098 (m, CH$_{arom}$, 7/10-H$_2$), 8.773 (s, CH$_{arom}$, 5/12-H$_2$), 8.831 (s, CH$_{arom}$, 6/11-H$_2$) ppm.

$^{13}$C-NMR (125 MHz, THF-d$_8$, 300 K): δ=24.62 (13/14-C), 127.21 (8/9-C), 128.23 (5/12-C), 128.35 (6/11-C), 129.89 (7/10-C), 133.23 (5'/11'-C), 133.84 (6'/10'-C), 139.87 (1'/4'-C), 156.71 (2/3-C) ppm.

EI-MS: m/z=258 (M$^+$)

Example 7—Acid-Catalysed Synthesis of the naptho[2,3-g]quinoxalines

In a 100 ml round bottom flask one equivalent of 2,3-diaminoanthracene were suspended in THF (25 ml for each 0.5 g 2,3-diaminoanthracene). Subsequently one equivalent of the respective di-ketone R$^{10}$—C(=O)—C(=O)—R$^{10}$ and 1 ml of glacial acetic acid were added. The reaction mixture was then stirred at the temperature indicated in Table 1 for the time indicated in Table 1, cooled in the dark and filtered. The filtrate was freed of solvent in a rotary evaporator. The so-obtained residue was extracted with n-hexane and in the following re-crystallized from toluene.

TABLE 1

| Example | R$^{10}$ | Temperature [° C.] | Time [min] | Yield [%] |
|---|---|---|---|---|
| 7.1 | CH$_2$Br | 70 | 20 | 90 |
| 7.2 | C$_6$H$_5$ | 70 | 30 | 88 |
| 7.3 | C$_6$H$_4$Br | 60 | 20 | 96 |

TABLE 1-continued

| Example | R¹⁰ | Temperature [°C.] | Time [min] | Yield [%] |
|---|---|---|---|---|
| 7.4 | C₆H₄F | 70 | 20 | 36 |
| 7.5 | C₆H₄OCH₃ | 76 | 50 | 77 |
| 7.6 | C₆H₄OH | 76 | 150 | 43 |
| 7.7 | 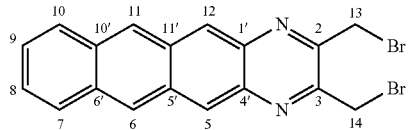 | 70 | 50 | 75 |

Example 7.1—2,3-Bis(bromomethyl)naphtho[2,3-q]quinoxaline

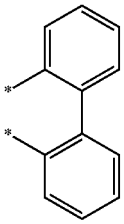

$^1$H-NMR (500 MHz, THF-d₈, 300 K): δ=5.077 (s, CH₂, 13/14-H₄), 1.7547 (m, CH$_{arom}$, 8/9-H₂), 8.150 (m, CH$_{arom}$, 7/10-H₂), 8.943 (s, CH$_{arom}$, 6/11-H₂), 8.960 (s, CH$_{arom}$, 5/12-H₂) ppm.

$^{13}$C-NMR (75 MHz, THF-d₈, 300 K): δ=32.85 (13/14-C), 127.96 (8/9-C), 129.00 and 129.82 (6/11/5/12-C), 130.01 (7/10-C), 133.87 (5'/11'-C), 134.50 (6'/10'-C), 139.09 (1'/4'-C), 153.21 (2/3-C) ppm.

EI-MS: m/z=416 (M⁺)

Example 7.2—2,3-Diphenylnaphtho[2,3-q]quinoxaline

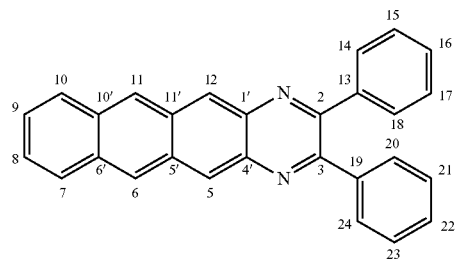

$^1$H-NMR (500 MHz, CD₂Cl₂, 300 K): δ=7.385 (m, CH$_{arom}$15/17/21/23-H₄), 7.431 (m, CH$_{arom}$, 16/22-H₂), 7.467 (m, CH$_{arom}$, 8/9-H₂), 7.591 (m, CH$_{arom}$, 14/18/20/24-H₄), 8.031 (m, CH$_{arom}$, 7/10-H₂), 8.748 (s, CH$_{arom}$, 6/11-H₂), 8.899 (s, CH$_{arom}$, 5/12-H₂) ppm.

$^{13}$C-NMR (75 MHz, CD₂Cl₂, 300 K): δ=126.77 (8/9-C), 127.75 (6/11-C), 128.46 (5/12-C), 128.85 (15/17/21/23-C), 129.00 (7/10-C), 129.802 (16/22-C), 130.64 (14/18/20/24-C) 132.67 (5'11'-C), 132.99 (6'/10'-C), 138.14 (1'/4'-C), 140.13 (13/19-C), 155.06 (2/3-C) ppm.

EI-MS: m/z=382 (M⁺)

Example 7.3—2,3-Bis(4-bromophenyl)naphtho[2,3-g]quinoxaline

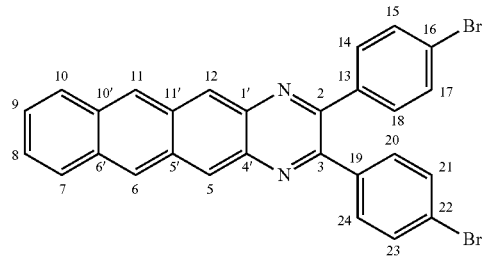

$^1$H-NMR (500 MHz, THF d₈, 300 K): δ=7.527 (m, CH$_{arom}$, 8/9-H₂), 7.619 (m, CH$_{arom}$, 14/15/17/18/20/21/23/24-H₈), 8.132 (m, CH$_{arom}$, 7/10-H₂), 8.916 (s, CH$_{arom}$, 4/11-H₂), 9.008 (s, CH$_{arom}$, 5/12-H₂) ppm.

$^{13}$C-NMR (125 MHz, THF d₈, 300 K): δ=125.25 (16/22-C), 127.75 (8/9-C), 128.82 (6/11-C), 129.57 (5/12-C), 129.99 (7/10-C), 133.03 and 133.50 (14/15/17/18/20/21/23/24-C), 133.93 (5'/11'-C), 134.34 (6'/10'-C), 139.15 (4'/1'-C), 140.23 (13/19-C), 154.48 (2/3-C) ppm.

Example 7.4—2,3-Bis(4-fluorphenyl)naphtho[2,3-q]quinoxaline

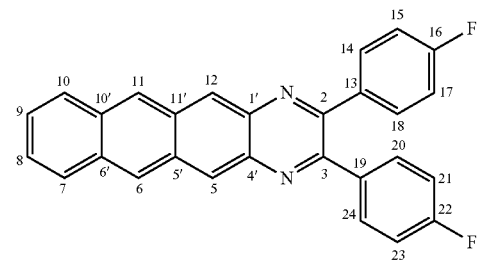

$^1$H-NMR (500 MHz, CDCl₃, 300 K): δ=7.091 (t, CH$_{arom}$, 15/17/21/23-H₄), 7.480 (m, CH$_{arom}$, 8/9-CH₂), 7.579 (m, CH$_{arom}$, 14/18/20/24-H₄), 8.045 (m, CH$_{arom}$, 7/10-H₂), 8.776 (s, CH$_{arom}$, 6/11-H₂), 8.968 (s, CH$_{arom}$, H₂) ppm.

$^{13}$C-NMR (125 MHz, CDCl₃, 300 K): δ=115.87 (d, $^2J_{(C,F)}$=21.35 Hz, 15/17/21/23-C), 126.51 (8/9-C), 127.49 (6/11-C), 128.19 (5/12-C), 128.64 (7/10-C), 132.15 (d, $^3J_{(C,F)}$=8.54 Hz, 14/18/20/24-C), 132.34 (5'/11'-C), 132.74 (6'/10'-C), 135.32 (13/19-C), 137.42 (1'/4'-C), 153.31 (2/3-C), 162.81 and 164.80 (d, $^1J_{(C,F)}$=250.45 Hz, 16/22-C) ppm.

EI-MS: m/z=418 (M⁺)

Example 7.5—2,3-Bis(4-methoxyphenyl)naphtho[2,3-q]quinoxaline

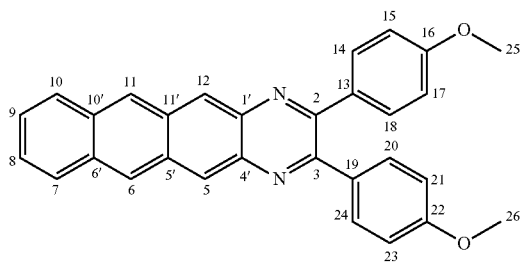

$^1$H-NMR (500 MHz, THF d$_8$, 300K): δ=3.879 (s, CH$_3$, 25/26-H$_6$), 6.969 (d, CH$_{arom}$, 15/17/21/23-H$_2$), 7.485 (m, CH$_{arom}$, 8/9-H$_2$), 7.662 (d, CH$_{arom}$, 14/18/20/24-H$_4$), 8.099 (m, CH$_{arom}$, 7/10-H$_2$), 8.844 (s, CH$_{arom}$, 6/11-H$_2$), 8.912 (s, CH$_{arom}$, 5/12-H$_2$) ppm.
$^{13}$C-NMR (125 MHz, THF d$_8$, 300K): δ=56.35 (25/26-C), 115.01 (15/17/21/23-C), 127.37 (8/9-C), 128.52 (6/11-C), 128.86 (5/12-C), 129.94 (7/10-C), 133.12 (14/18/20/24-C), 133.75 (5'11'-C), 133.89 (13/19-C), 134.05 (6'/10'-C), 139.38 (1'/4'-C), 155.49 (2/3-C), 162.55 (16/22-C) ppm.
EI-MS: m/z=442 (M$^+$)

Example 7.6—2,3-Bis(4-hydroxyphenyl)naphtho[2,3-q]quinoxaline

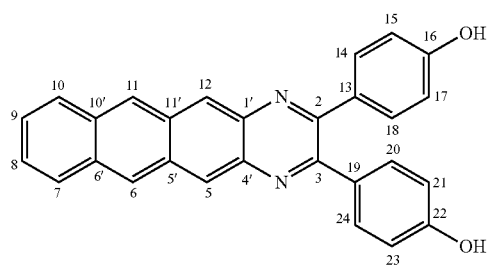

$^1$H-NMR (500 MHz, THF d$_8$, 300K): δ=6.811 (d, CH$_{arom}$, 15/17/21/23-H$_4$), 7.478 (m, CH$_{arom}$, 8/9-H$_2$), 7.593 (d, CH$_{arom}$, 14/18/20/24-H$_4$), 8.097 (m, CH$_{arom}$, 7/10-H$_2$), 8.633 (s, OH; H$_2$), 8.840 (s, CH$_{arom}$, 6/11-H$_2$), 8.886 (s, CH$_{arom}$, 5/12-H$_2$) ppm.
$^{13}$C-NMR (125 MHz, THF d$_8$, 300K): δ 116.47 (15/17/21/23-C), 127.32 (8/9-C), 128.47 (6/11-C), 128.65 (5/12-C), 129.96 (7/10-C), 132.76 (13/19-C), 133.25 (14/18/20/24-C), 133.71 (5'/11'-C), 133.99 (6'/10'-C), 139.47 (1'/4'-C), 155.76 (2/3-C), 160.69 (16/22-C) ppm.
EI-MS: m/z=414 (M+)

Example 7.7—Dibenzo[a,c]naphtho[2,3-i]phenazine

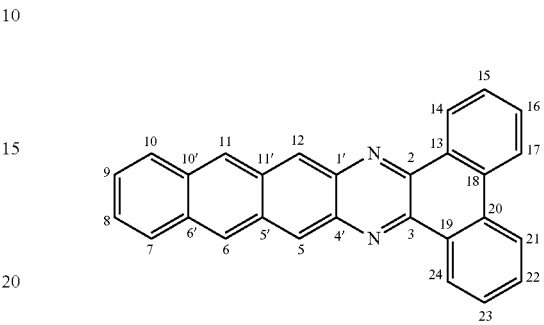

$^1$H-NMR (500 MHz, THF-d$_8$, 300K): δ=7.36 (dd, CH$_{arom}$, 8/9-H$_2$), 7.60 (m, CH$_{arom}$, 15/16/22/23-H$_4$), 7.99 (dd, CH$_{arom}$, 7/10), 8.52 (d, CH$_{arom}$, 14/24-H$_2$), 8.85 (s, CH$_{arom}$, 5/12-H$_2$), 9.10 (s, CH$_{arom}$, 6/11-H$_2$), 9.29 (dd, CH$_{arom}$, 17/21-H$_2$) ppm.
EI-MS: m/z=380 (M$^+$)

Example 8—Synthesis of a Phosphorous Acid Ester

Example 8.1—Synthesis of 1,2-bis(4-[3'-diethoxyphosphoryl]propoxyphenyl)-ethane-1,2-dione

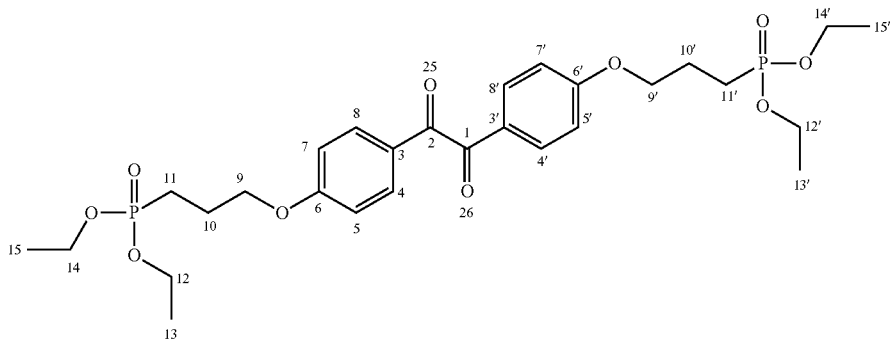 [SMILES: CCOP(=O)(CCCOc1ccc(C(=O)C(=O)c2ccc(OCCCP(=O)(OCC)OCC)cc2)cc1)OCC]

In a 100 ml three neck flask with a dropping funnel 0.500 g (0.0021 mol, 1 eq.) 4,4'-dihydroxybenzil and 1.340 g (0.0041 mol, 2 eq.) CsCO$_3$ were degassed and put under argon atmosphere. Subsequently 15 ml water-free DMF were added and the resulting mixture stirred at 20° C. for 15 min. A solution of 1.065 g (0.0041 mol, 2 eq.) (3-bromopropyl)phosphorous acid diethylester in 2.5 ml water-free DMF were slowly added dropwise. After stirring at 20° C. overnight 25 ml dichloromethane and 25 ml distilled water were added and the organic phase sequentially washed with aqueous NaOH and distilled water. The aqueous phase was extracted twice with dichloromethane, the combined organic phases dried over magnesium sulfate and the solvent removed in vacuo, thus yielding 0.987 g (0.0016 mol, 76%) of the desired product.

$^1$H-NMR (500 MHz, CDCl$_3$, 300 K): δ=1.284 (t, CH$_3$, 13/13'/15/15'-H$_{12}$), 1.899 (m, CH$_2$, 11/11'-H$_4$), 2.085 (m, CH$_2$, 10/10'-H$_4$), 4.065 (m, CH$_2$, 9/9'/12/12'/14/14'-H$_{12}$), 6.912 (d, CH$_{arom}$, 7/7'-H$_4$), 7.885 (d, CH$_{arom}$, 8/8'-H$_4$) ppm.

$^{13}$C-NMR (125 MHz, CDCl$_3$, 300 K): δ=16.69 ($^3J_{(CP)}$=5.9 Hz, 13/13'/15/15'-C), 21.84 and 22.98 ($^1J_{(CP)}$=142.75 Hz, 11/11'-C), 22.74 ($^2J_{(CP)}$=4.46 Hz, 10/10'-C), 62.02 ($^2J_{(CP)}$=6.75 Hz, 12/12'/14/14'-C), 67.98 ($^3J_{(CP)}$=15.96 Hz, 9/9'-C), 114.99 (7/7'-C), 126.64 (3/3'-C), 132.62 (8/8'-C), 164.28 (6/6'-C), 193.67 (1/2-C) ppm.

Example 8.2—Synthesis of 2,3-bis(4-[3'-diethoxy-phosphinyl]propoxyphenyl)-naphtho[2,3-g]quinoxaline

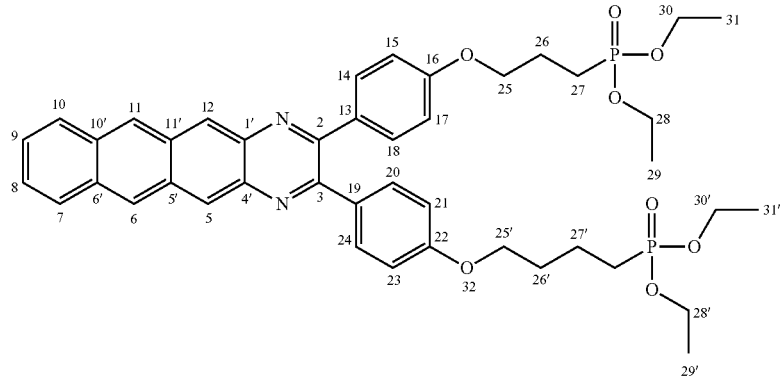 [SMILES: CCOP(=O)(CCCCOc1ccc(-c2nc3cc4cc5ccccc5cc4cc3nc2-c2ccc(OCCCP(=O)(OCC)OCC)cc2)cc1)OCC]

To a solution of 0.891 g (0.0015 mol, 1 eq.) 1,2-bis(4-[3'-diethoxyphos-phoryl]propoxyphenyl)-ethane-1,2-dione in 30 ml THF in a 100 ml round bottom flask were added 0.309 g (0.0015 mol, 1 eq.) 2,3-diaminoanthracene, followed by the addition of 1 ml of glacial acetic acid. Following heating to 70° C. for 25 min the solvent was removed by distillation. The so-obtained residue was taken up in dichloromethane and extracted twice with distilled water. The aqueous phase was then extracted with dichloromethane and the combined organic phases dried over MgSO$_4$. After removal of the solvent 0.983 g (0.0013 mol, 85%) of the desired product were obtained.

$^1$H-NMR (500 MHz, CDCl$_3$, 300 K): δ=1.259 (t, CH$_3$, 29/29'/31/31'-H$_{12}$), 1.891 (m, CH$_2$, 27.27'-H$_4$), 1.997-2.065 (m, CH$_2$, 26/26'-H$_4$), 3.664-3.962 (m, CH$_2$, 25/25'-H$_4$), 4.012-4.099 (m, CH$_2$, 28/28'30/30'-H$_8$), 6.791 (m, CH$_{arom}$, 15/17/21/23-H$_4$), 7.351 (m, CH$_{arom}$, 8/9-H$_2$), 7.457 (d, CH$_{arom}$, 14/18/20/24-H$_4$), 7.918 (m, CH$_{arom}$, 7/10-H$_2$), 8.621 (s, CH$_{arom}$, 6/11-H$_2$), 8.788 (s, CH$_{arom}$, 5/12-H$_2$) ppm.

$^{13}$C-NMR (125 MHz, CDCl$_3$, 300 K): δ=16.77 (29/29'31/31'-C), 22.01 and 23.15 ($^1J_{(CP)}$=143.5 Hz, 27/27'-C), 22.94 ($^2J_{(CP)}$=4.79 Hz, 26/26'-C), 62.14 ($^2J_{(CP)}$=6.14 Hz, 28/28'/30/30'-C), 67.68 ($^3J_{(CP)}$=16.42 Hz, 25/25'-C), 114.55 (15/17/21/23-C), 126.17 (8/9-C), 127.23 (6/11-C), 127.65 (5/12-C), 128.56 (7/10-C), 131.66 (14/18/20/24-C), 132.14 (5'/11'-C), 132.19 (13/19-C), 132.44 (6'/10'-C), 137.63 (1'/4'-C), 154.22 (2/3-C), 159.96 (16/22-C) ppm.

Example 8.3—Synthesis of 2,3-bis(4-[3'-dihydroxy-phosphinyl]propoxyphenyl)-naphtho[2,3-g]quinoxaline

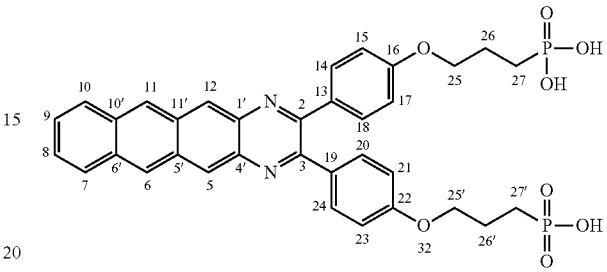

In a 100 ml three necked flask (0.0006 mol, 1 eq.) 2,3-bis(4-[3'-diethoxyphosphinyl]propoxyphenyl)-naphtho[2,3-g]quinoxaline were degassed and under argon atmosphere dissolved in 30 ml water-free chloroform. Then 1.5 ml (1.68 g, 0.0109 mol, 18 eq.) bromotrimethylsilane were added dropwise. The reaction mixture was stirred at 20° C. overnight in the dark, followed by the addition of 200 ml distilled water. Subsequently the mixture was filtered and the obtained residue washed with distilled water and n-hexane. The so-obtained product was then dried resulting in 0.2 g (0.0003 mol, 50%) 2,3-bis(4-[3'-dihydroxyphosphinyl]propoxyphenyl)-naphtho[2,3-g]quinoxaline.

$^1$H-NMR (500 MHz, DMSO-d$_6$, 300 K): δ=1.701-1.769 (m, CH$_2$, 27/17'-H$_4$), 1.935-2.016 (m, CH$_2$, 26/26'-H$_4$), 4.117 (m, CH$_2$, 25/25'-H$_4$), 6.991 (d, CH$_{arom}$, 15/17/21/23-H$_4$), 7.524-7.566 (m, CH$_{arom}$, 8/9/14/18/20/24-H$_6$), 8.141 (m, CH$_{arom}$, 7/10-H$_2$), 8.962 (m, CH$_{arom}$, 5/6/11/12-H$_4$) ppm.

$^{13}$C-NMR (125 MHz, DMSO-d$_6$, 300 K): δ=23.77 ($^2J_{(CP)}$=3.33 Hz, 26/26'-C), 24.38 and 25.48 ($^1J_{(CP)}$=137.59 Hz, 27/27'-H$_4$), 68.54 ($^3J_{(CP)}$=16.68 Hz, 25/25'-C), 114.98 (15/17/21/23-C), 127.06 (8/9-C), 127.72/127.83 (5/6/11/12-C), 129.06 (7/10-C), 132.14-132.20 (5'/11'/13/14/18/19/20/24), 132.55 (6'10'-C), 137.65 (1'/4'-C), 154.56 (2/3-C), 160.28 (16/22-C) ppm.

ESI-MS: m/z=659 [M+H]$^+$

Example 9—Synthesis of 2,3-dimethylpyrazino[2,3-b]phenazine

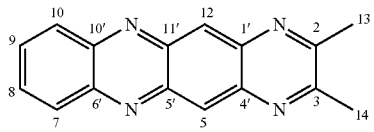

In a 100 ml round bottom flask 0.81 g (3.8 mmol, 1 eq.) 2,3-diaminophenazine were suspended in 50 ml THF and then 2 ml glacial acetic acid added, followed by the addition of 3.5 ml (40 mmol, 10 eq.) 2,3-butanedione. The reaction mixture was stirred at 70° C. for 2 hours, during which time a dark-yellow solid precipitated. The reaction mixture was then cooled to room temperature and the solid collected by filtration. The yellow solid was washed with methanol and THF, yielding 0.615 g (2.4 mmol, 62%) 2,3-diaminophenazine.

$^1$H-NMR (500 MHz, CDCl$_3$, 300 K): δ=2.845 (s, CH$_3$, 13/14-H$_6$), 7.857 (m, CH$_{arom}$, 8/9-H$_2$), 8.273 (m, CH$_{arom}$, 7/10-H$_2$), 9.009 (s, CH$_{arom}$, 5/12-H$_2$) ppm.

$^{13}$C-NMR (125 MHz, CDCl$_3$, 300 K): δ=24.33 (13/14-C), 128.41 (5/12-C), 130.29 (7/10-C), 131.62 (8/9-C), 140.81 (1'/4'-C), 141.99 (11'5'-C), 145.21 (6'/10'-C), 157.02 (2/3-C) ppm.

EI-MS: m/z=260 (M$^+$)

Example 10—Synthesis of pyrazino[2,3-b]phenazines in methanol

In a 100 ml two necked flask one equivalent 2,3-diaminophenazine was suspended in methanol (55 ml methanol for each 0.5 g 2,3-diaminophenazine).

Subsequently one equivalent of the respective di-ketone R$^{11}$—C(=O)—C(=O)—R$^{11}$ and 2 ml of glacial acetic acid were added. The resulting reaction mixture was stirred at the temperature indicated in Table 2 for the time indicated in Table 2, during which time the desired product precipitated. The product was collected by filtration and washed with methanol.

TABLE 2

| Example | R$^{11}$ | Temperature [° C.] | Time [min] | Yield [%] |
|---|---|---|---|---|
| 10.1 | CH$_2$Br | 70 | 45 | 18 |
| 10.2 | C$_6$H$_5$ | 70 | 360 | 65 |
| 10.3 | C$_6$H$_4$F | 70 | 47 | 72 |
| 10.4 | C$_6$H$_4$CF$_3$ | 70 | 30 | 53 |
| 10.5 | ![biphenyl] | 70 | 390 | 40 |

Example 10.1—2,3-Bis(bromomethyl)pyrazino[2,3-b]phenazine

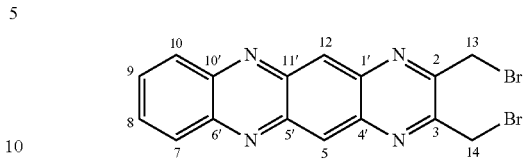

$^1$H-NMR (500 MHz, THF-d$^8$, 300K): δ=4.961 (s, CH$_2$, 13/14-H$_4$), 7.825 (m, CH$_{arom}$, 8/9-H$_2$), 8.158 (m, CH$_{arom}$, 7/10-H$_2$), 8.953 (s, CH$_{arom}$, 5/12-H$_2$) ppm.

EI-MS: m/z=418 (M$^+$)

Example 10.2—2,3-Diphenylpyrazino[2,3-b]phenazine

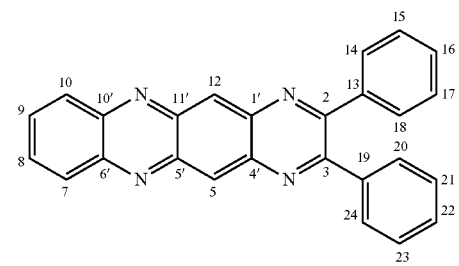

$^1$H-NMR (500 MHz, CDCl$_3$, 300 K): δ=7.394 (t, CH$_{arom}$, 15/17/21/23-H$_4$), 7.445 (t, CH$_{arom}$, 16/22-H$_2$), 7.638 (d, CH$_{arom}$, 14/18/20/24-H$_4$), 7.863 (m, CH$_{arom}$, 8/9-H$_2$), 8.281 (m, CH$_{arom}$, 7/10-H$_2$), 9.214 (s, CH$_{arom}$, 5/12-H$_2$) ppm.

$^{13}$C-NMR (125 MHz, CDCl$_3$, 300 K): δ=128.69 (15/17/21/23-C), 129.53 (5/12-C), 130.03 (16/22-C), 130.29 (14/18/20/24-C), 130.39 (7/10-C), 131.85 (8/9-C), 138.99 (13/19-C), 140.48/142.52 (1'/4'/5'/11'-C), 145.49 (6'/10'-C), 156.27 (2/3-C) ppm.

EI-MS: m/z=384 (M$^+$)

Example 10.3—2,3-Bis(4-fluorophenyl)pyrazino[2,3-b]phenazine

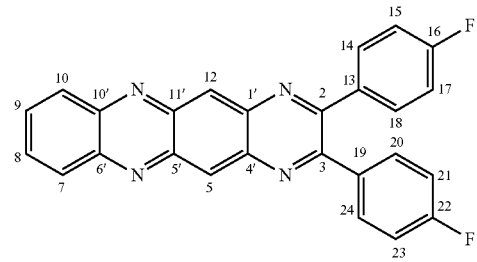

$^1$H-NMR (500 MHz, CDCl$_3$, 300 K): δ=7.115 (m, CH$_{arom}$, 15/17/21/23-H$_4$), 7.637 (m, CH$_{arom}$, 14/18/20/24-H$_4$), 7.874 (m, CH$_{arom}$, 8/9-H$_2$), 8.285 (m, CH$_{arom}$, 7/10-H$_2$), 9.196 (s, CH$_{arom}$, 5/12-H$_2$) ppm.

$^{13}$C-NMR (125 MHz, THF d$^8$, 300K): δ=116.04 (d, $^2$J$_{(C,F)}$=21.54 Hz, 15/17/21/23-C), 129.52 (5/12-C), 130.35

(7/10-C), 132.05 (8/9-C), 132.38 (d, $^3J_{(C,F)}$=8.45 Hz, 14/18/20/24-C), 134.92 (d, $^4J_{(C,F)}$=3.73 Hz, 13/19-C), 140.32 and 142.52 (1'/4'/5'/11'-C), 145.60 (6'10'-C), 154.89 (2/3-C), 163.16 and 165.14 (d, $^1J_{(C,F)}$=251.04 Hz, 16/22-C) ppm.

Example 10.4—2,3-Bis(4-(trifluoromethyl)phenyl)pyrazino[2,3-b]phenazine

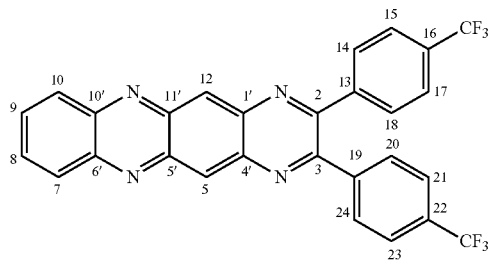

$^1$H-NMR (500 MHz, CDCl$_3$, 300 K): δ=7.699 (d, CH$_{arom}$, 15/17/21/23-H$_4$), 7.770 (d, CH$_{arom}$, 14/18/20/24-H$_4$), 7.905 (m, CH$_{arom}$, 8/9-H$_2$), 8.300 (m, CH$_{arom}$, 7/10-H$_2$), 9.272 (s, CH$_{arom}$, 5/12-H$_2$) ppm.

$^{13}$C-NMR (125 MHz, CDCl$_3$, 300 K): δ=123.18 (CF$_3$-C), 125.93 (15/17/21/23-C), 130.10 (5/12-C), 130.38 (7/10-C), 130.66 (14/18/20/24-C), 132.32 (16/22-C), 132.39 (8/9-C), 140.11 (5'11'-C), 141.93 (13/19-C), 142.58 (1'/4'-C), 145.76 (6'10'-C), 154.22 (2/3-C) ppm.

Example 10.5—Dibenzo[a,c]quinoxalino[2,3-i]phenazine

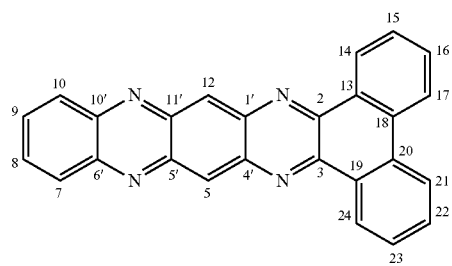

$^1$H-NMR (500 MHz, CDCl$_3$, 300 K): δ=7.672-7.831 (m, CH$_{arom}$, 8/9/15/16/22/23-H$_6$), 8.237 (m, CH$_{arom}$, 7/10-H$_2$), 8.440 (dd, CH$_{arom}$, 14/24-H$_2$), 9.345 (s, CH$_{arom}$, 5/12-H$_2$), 9.389 (dd, CH$_{arom}$, 17/21-H$_2$) ppm.

EI-MS: m/z=382 (M$^+$)

Elementary analysis: C: 81.66 N: 14.65 H: 3.69 (calculated)
C: 81.05 N: 14.58 H: 3.77 (found)

Example 11—Synthesis of Octafluorophenazine

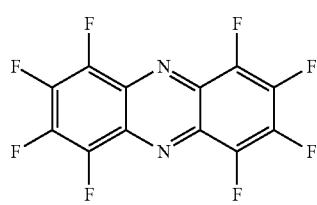 [SMILES: Fc1c(F)c(F)c2nc3c(F)c(F)c(F)c(F)c3nc2c1F]

To a solution of 10.0 g (0.055 mol) pentafluoroaniline in 300 ml toluene in a 500 ml three necked flask with reflux condenser were added 50.0 g (0.113 mol) lead(IV) acetate (lead tetraacetate). The reaction mixture was then heated to reflux for 1 hour, cooled and subsequently washed with 50% acetic acid, distilled water, saturated aqueous NaHCO$_3$ solution and saturated aqueous NaCl solution. The organic phase was dried over MgSO$_4$, filtered and the solvent removed in vacuo. The crude product was purified by column chromatography with a mixture of toluene and cyclohexane in a 1:1 volumetric ratio, yielding 1.5 g (17%) of the yellow product.

R$_f$: 0.43 (Toluol/Cyclohexan 1:1)

$^{19}$F-NMR (282 MHz, CDCl$_3$, 300K): δ=−149.52 (m, 4F, CF); −146.61 (m, 4F, CF) ppm.

$^{13}$C-NMR (125 MHz, CDCl$_3$, 300K): δ=131.45 (4C, C$_{quartär}$); 140.23/141.64/142.34/143.74 (8C, CF) ppm.

EI-MS: m/z=324 (M$^+$)

Example 12—Synthesis of 5,7,8,9,10,12-hexafluoro-2,3-diphenylpyrazino[2,3-b]phenazine Example 12.1—Synthesis of 1,2-diphenyl-1,2-ditosyloxyethane

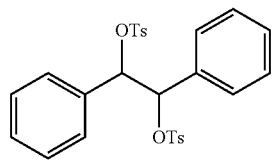 [SMILES: Cc1ccc(S(=O)(=O)OC(c2ccccc2)C(OS(=O)(=O)c2ccc(C)cc2)c2ccccc2)cc1]

In a 250 ml three necked flask with reflux condenser and dropping funnel 15.0 g (0.07 mol) meso-hydrobenzoin (meso-1,2-diphenyl-1,2-ethanediol) were degassed and dissolved in 45 ml water-free pyridine. At 0° C. a solution of 32.0 g (0.17 mol) p-toluenesulfonyl chloride (H$_3$C—C$_6$H$_4$—SO$_2$Cl) in 33 ml water-free pyridine was slowly added dropwise. The reaction mixture was then stirred at room temperature for 94 hours, poured into 200 ml ice water and three times extracted with dichloromethane. The organic phase was washed subsequently with diluted hydrochloric acid (10%), saturated aqueous NaHCO$_3$ solution and distilled water, and then dried over MagSO$_4$. The solvent was removed by distillation and the crude product washed with a mixture of dichloromethane and cyclohexane in a 1:1 volumetric ratio, yielding 24.16 g (66%) of the desired product.

$^1$H-NMR (300 MHz, CDCl$_3$, 300K): δ=2.29 (s, 6H, CH$_3$); 5.49 (s, 2H, CH); 6.87 (d, 4H, CH$_{arom}$); 7.05 (m, 8H, CH$_{arom}$); 7.15 (m, 2H, CH$_{arom}$); 7.38 (d 4H, CH$_{arom}$) ppm.

$^{13}$C-NMR (75 MHz, CDCl$_3$, 300K): δ=21.92 (2C, CH$_3$); 83.82 (2C, CH); 128.09/128.13/128.40/129.26/129.83 (18C, CH$_{arom}$); 133.85/144.87 (6C, C$_{quart}$) ppm.

Example 12.2—Synthesis of 1,2-diphenylethane-1,2-diazide

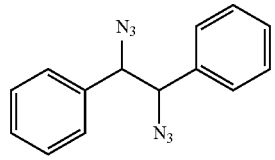 [SMILES: [N-]=[N+]=NC(c1ccccc1)C(N=[N+]=[N-])c1ccccc1]

In a 500 ml round bottom flask 24.16 g (0.05 mol) 1,2-Diphenyl-1,2-ditosyloxyethane and 7.80 g (0.12 mol) sodium azide were stirred at 90° C. for 5 hours in 250 ml dimethylformamide. After allowing the reaction mixture to cool to room temperature 500 ml distilled water were added. The resulting mixture was extracted four times with diethylether. The combined organic phases were then washed with distilled water, dried over MgSO$_4$ and the solvent removed by distillation, yielding an oil that crystallized upon being allowed to stand, resulting in 4.32 g (36%) 1,2-diphenylethane-1,2-diazide.

$^1$H-NMR (500 MHz, CDCl$_3$, 300K): δ=4.61 (s, 2H, CH); 7.18-7.20 (m, 4H, CH$_{arom}$); 7.28-7.33 (m, 6C, CH$_{arom}$) ppm.

$^{13}$C-NMR (125 MHz, CDCl$_3$, 300K): δ=70.04 (2C, CH); 128.30 (4C, CH); 129.04 (4C, CH); 129.20 (2C, CH) 136.24 (2C; C$_{quart}$) ppm.

Example 12.3—Synthesis of 1,2-diphenylethane-1,2-diamine

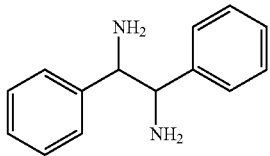 [SMILES: NC(c1ccccc1)C(N)c1ccccc1]

In a 500 ml three necked flask with reflux condenser and dropping funnel 5.11 g (0.14 mol) LiAlH$_4$ were suspended in 100 ml water-free diethylether. Then a solution of 4.32 g (0.02 mol) 1,2-diphenylethane-1,2-diazide in 150 ml diethylether was added dropwise. The reaction mixture was stirred first under reflux for 2 hours and then for an additional 12 hours at room temperature, followed by the cautious addition of distilled water to remove any unreacted LiAlH$_4$. The resulting mixture was then filtered, the filtrate dried over MgSO$_4$ and the solvent removed using a rotary evaporator. The so-obtained crude solid was re-crystallized from n-hexane, yielding 1.27 g (37%) 1,2-diphenylethane-1,2-diamine.

$^1$H-NMR (500 MHz, CDCl$_3$, 300K): δ=1.35 (s$_{breit}$, 4 H, NH$_2$); 4.02 (s, 2H, CH); 7.19-7.23 (m, 2H, CH$_{arom}$); 7.26-7.32 (m, 8H, CH$_{arom}$) ppm.

$^{13}$C-NMR (125 MHz, CDCl$_3$, 300K): δ=63.19 (2C, CH); 127.97 (6C, CH$_{arom}$); 128.79 (4C, CH$_{arom}$); 143.31 (2C, C$_{quart}$) ppm.

Example 12.4—Synthesis of 5,7,8,9,10,12-hexafluoro-2,3-diphenyl-1,2,3,4-tetrahydropyrazino[2,3-b]phenazine

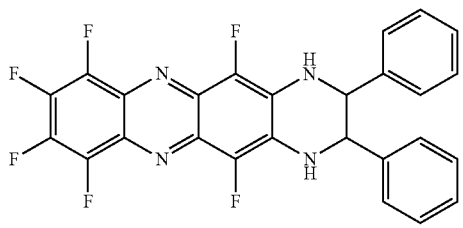 [SMILES: Fc1c(F)c(F)c2nc3c(F)c4c(c(F)c3nc2c1F)NC(c1ccccc1)C(c1ccccc1)N4]

To 0.91 g (0.003 mol) octafluorophenazine in 120 ml dimethylformamide in a 250 ml round bottom flask were added subsequently 0.31 g (0.003 mol) triethylamine and 0.71 g (0.003 mol) 1,2-diphenylethane-1,2-diamine. After 19 hours of stirring at room temperature, during which a red solid precipitated, the reaction mixture was poured into 500 ml distilled water and extracted twice with ethyl acetate. The combined organic phases were dried over MgSO$_4$ and the solvent removed by distillation. The so-obtained solid was re-crystallized from chloroform, yielding 1.20 g (86%) 5,7,8,9,10,12-hexafluoro-2,3-diphenyl-1,2,3,4-tetrahydropyrazino[2,3-b]phenazine.

$^{19}$F-NMR (282 MHz, THF-d$^8$, 300 K): δ=-156.13 (m, 2F, CF); -160.6 (m, 2F, CF); -161.65 (s, 2F, CF) ppm.

$^1$H-NMR (500 MHz, THF-d$^8$, 300K): δ=4.92 (s, 2H, CH); 6.81 (d, 4H, CH$_{arom}$); 7.01 (t, 4H, CH$_{arom}$); 7.06 (t, 2H, CH$_{arom}$); 7.27 (s$_{breit}$, 2 H, NH) ppm.

$^{13}$C-NMR (125 MHz, THF-d$^8$, 300K): δ=60.19 (2C, CH); 129.43 (6C, CH$_{arom}$); 129.80 (4C, CH$_{arom}$); 131.42 (2C, C$_{quart}$); 136.56-138.57 (d, 2C, CF); 140.43 (2C, C$_{quart}$) ppm.

EI-MS: m/z=496 (M$^+$)

Example 12.5—Synthesis of 5,7,8,9,10,12-hexafluoro-2,3-diphenylpyrazino[2,3-b]phenazine (HFDPPP)

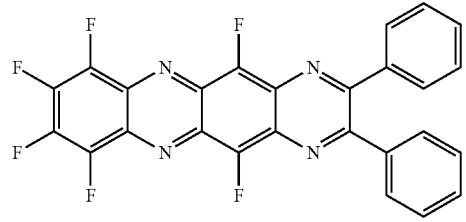 [SMILES: Fc1c(F)c(F)c2nc3c(F)c4nc(-c5ccccc5)c(-c5ccccc5)nc4c(F)c3nc2c1F]

In a 250 ml three necked flask with reflux condenser 0.90 g (0.002 mol) 5,7,8,9,10,12-hexafluoro-2,3-diphenyl-1,2,3,4-tetrahydropyrazino[2,3-b]phenazine were degassed and suspended in 70 ml water-free xylene. To the resulting orange-colored suspension were added 4.11 g (0.018 mol) 1,2-dichloro-5,6-dicyano-1,4-benzoquinone. After stirring at 130° C. for 30 minutes the reaction mixture was allowed to cool to room temperature. Then 30 ml ethyl acetate was added. Subsequently the crude product was collected by filtration and washed with hot THF, yielding 0.32 g (36%) crude 5,7,8,9,10,12-hexafluoro-2,3-diphenylpyrazino[2,3-b]phenazine, which was further purified by sublimation at a pressure of 10$^{-3}$ mbar and a temperature of 215° C.

$^{19}$F-NMR (282 MHz, THF-d$^8$, 300K): δ=-135.95 (s, 2F; CF); -150.89 (m, 2F, CF); -153.34 (m, 2F, CF) ppm.

$^1$H-NMR (500 MHz, THF-d$^8$, 300K): δ=7.28 (t, 4H, CH$_{arom}$); 7.36 (t, 2H, CH$_{arom}$); 7.61 (d, 4H, CH$_{arom}$) ppm.

$^{13}$C-NMR (125 MHz, THF-d$^8$, 300K): δ=129.89 (4C, CH$_{arom}$); 129.98 (2C, CH$_{arom}$); 131.98 (4C, CH$_{arom}$) ppm.

EI-MS: m/z=492 (M$^+$)

Example 13

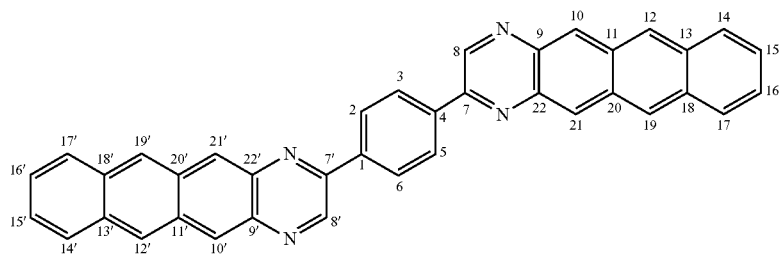 [SMILES: c1ccc2cc3cc4nc(-c5ccc(-c6cnc7cc8cc9ccccc9cc8cc7n6)cc5)cnc4cc3cc2c1]

In a 100 mL three necked flask 0.182 g (0.0010 mol, 1.0 Eq) 1,4-phenyl-diglyoxal and 0.43 g (0.0021 mol, 2.1 Eq) 2,3-diaminoanthracene were suspended in 25 mL THF and 1 mL acetic acid. The mixture was stirred for 30 minutes at 70° C. Afterwards the mixture was cooled to room temperature and filtered. The residue was washed with THF. 0.4 g (78%) of the product could be isolated.

EI-MS: m/z=534 (M$^+$)

Example 14

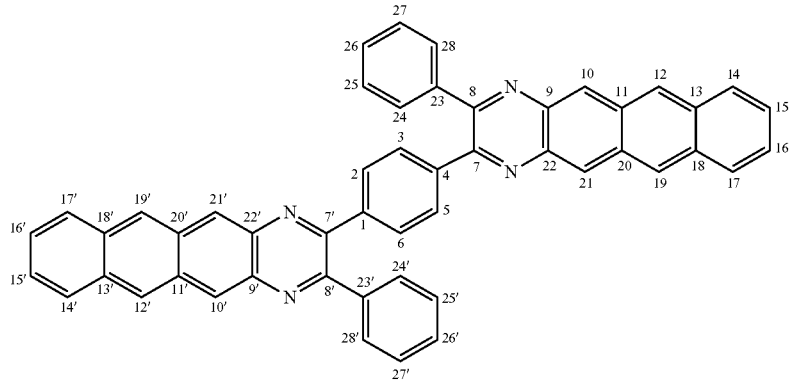 [SMILES: c1ccc(-c2nc3cc4cc5ccccc5cc4cc3nc2-c2ccc(-c3nc4cc5cc6ccccc6cc5cc4nc3-c3ccccc3)cc2)cc1]

In a 100 mL three necked flask 0.280 g (0.0013 mol, 2.1 Eq) 2,3-diaminoanthracene and 0.215 g (0.0006 mol, 1.0 Eq) 2,2'-(1,4-diphenylen)bis(1-phenylethane-1,2-dione) are suspended in 30 mL THF and 1 mL acetic acid. The mixture is stirred for 20 minutes at 70° C. Afterwards the mixture is allowed to cool to room temperature. The mixture is filtrated and the collected crude product is washed with boiling THF and crystallized from toluene. 0.186 g (42%) of the product can be isolated.

EI-MS: m/z=686 (M$^+$)

Example 15

Example 15.1—Synthesis of 4-bromo-4'-phenylbenzil

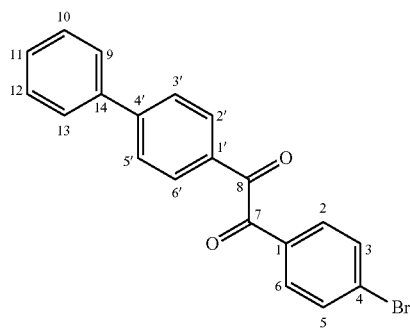

Under argon atmosphere 2.0 g (0.0054 mol, 1.0 Eq) 4,4'-dibromobenzil and 0.66 g (0.0054 mol, 1.1 Eq) phenylboronic acid were dissolved in 120 ml of a mixture of toluene and 1 M $K_2CO_3$ (aq) (1:1). Afterwards 0.3 g Pd(PPh$_3$)$_4$ were added. After stirring at 110° C. for 20 hours the mixture was allowed to cool to room temperature. The reaction mixture was extracted three times with diethyl ether and the organic phase was dried over MgSO$_4$. Evaporation of the solvent gave 2.32 g of the yellow crude product. After column chromatography (cyclohexane:chloroform 1:1) 0.920 g (46%) of the product could be isolated.

$^1$H-NMR (500 MHz, CD$_2$Cl$_2$, 300 K): δ=7.36 (t, CH$_{arom}$, 11-H$_1$), 7.42 (t, CH$_{arom}$, 10/12-H$_2$), 7.59 (d, CH$_{arom}$, 9/13-H$_2$), 7.63 (d, CH$_{arom}$, 3/5-H$_2$), 7.70 (d, CH$_{arom}$, 3'/5'-H$_2$), 7.80 (d, CH$_{arom}$, 2,6-H$_2$), 7.96 (m, CH$_{arom}$, 2'/6'-H$_2$) ppm.

$^{13}$C-NMR (125 MHz, CD$_2$Cl$_2$, 300 K): δ=128.16 (9/13-C), 128.47 (3'/5'-C), 129.54 (11-C), 129.88 (10/12-C), 131.16 (4-C), 131.27 (2'/6'-C), 132.07 (2/6-C), 132.37 (1'-C), 132.72 (1-C), 133.27 (2/4-C), 140.20 (14-C), 148.52 (4'-C), 194.21 (7-C), 194.31 (8-C) ppm.

EI-MS: m/z=364/265/366 (M$^+$)

Example 15.2—Synthesis of 4-p-Vinylphenyl-4'-phenylbenzil

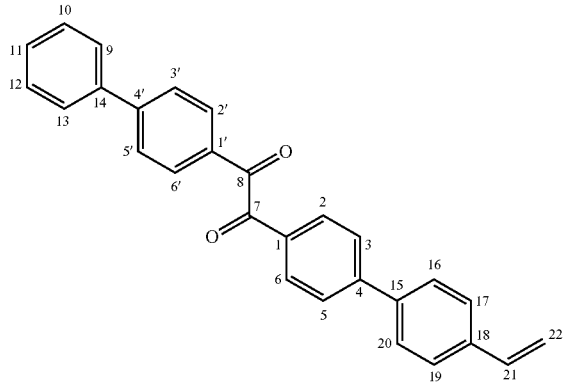 [SMILES: C=Cc1ccc(-c2ccc(C(=O)C(=O)c3ccc(-c4ccccc4)cc3)cc2)cc1]

Under argon atmosphere 0.89 g (0.0024 mol, 1.0 Eq) 4-bromo-4'-phenylbenzil and 0.39 g (0.0027 mol, 1.1 Eq) 4-viny-phenylboronic acid were dissolved in 60 ml of a mixture of toluene and 1 M $K_2CO_3$ (aq) (1:1). Afterwards 0.3 g $Pd(PPH_3)_4$ were added and the mixture was stirred at 110° C. for 20 hours. The reaction mixture was allowed to cool to room temperature and then was extracted with diethyl ether. The organic phase was dried over $MgSO_4$. Evaporation of the solvent gave 1.11 g of the yellow crude product. Further purification was done by column chromatography (cyclohexane:chloroform 1:1). Thus 0.88 g (93%) of the product were isolated.

$^1$H-NMR (500 MHz, $CD_2Cl_2$, 300 K): δ=5.33 (d, $CH_{2,trans}$, 22-$H_1$), 5.85 (d, $CH_{2,cis}$, 22-$H_1$), 6.79 (dd, $CH_2$, 21-$H_1$), 7.44 (m, $CH_{arom}$, 11-$H_1$), 7.50 (m, $CH_{arom}$, 10/12-$H_2$), 7.54 (m, $CH_{arom}$, 9/13-$H_2$), 7.66 (m, $CH_{arom}$, 16/17/19/20-$H_4$), 7.79 (m, $CH_{arom}$, 3/3'/5/5'-$H_4$), 8.07 (m, $CH_{arom}$, 2/2'/6/6'-$H_4$) ppm.

$^3J_{21,cis-22}$=17.6 Hz, $^3J_{21,trans-22}$=10.9 Hz.

$^{13}$C-NMR (125 MHz, $CD_2Cl_2$, 300 K): δ=115.22 (22-C), 127.44 (17/19-C), 128-127.93 (3/3'/6/6'/9/13/16/20-C), 129.25 (11-C), 129.62 (10/13-C), 131.04-131.01 (2/5/2'/5'-C), 132.40-132.39 (1/1'-C), 138.65 (18-C), 139.25 (15-C), 140.05 (14-C), 147.55 (4'-C), 148.12 (4-C), 194.79-194.74 (7/8-C) ppm.

Example 15.3

In a 100 mL three necked flask 0.34 g (0.0017 mol, 1.0 Eq) 2,3-diaminoanthracene and 0.67 g (0.0017 mol, 1.0 Eq) 4-p-vinylphenyl-4'-phenylbenzil were suspended in 30 mL THF and 1 mL acetic acid. The mixture is stirred for 20 minutes at 70° C. Afterwards the mixture was allowed to cool to room temperature and the solvent was evaporated. The crude product was purified by column chromatography (chloroform). 0.91 g (94%) of the product could be isolated.

$^1$H-NMR (500 MHz, $CDCl_3$, 300 K): δ=5.20 (d, $CH_{2,cis}$, 34-$H_1$), 5.71 (d, $CH_{2,trans}$, 34-$H_1$), 6.68 (dd, $CH_2$, 33-$H_1$), 7.28 (t, $CH_{arom}$, 20-$H_1$), 7.41-7.35 (m, $CH_{arom}$, 8/9/19/21/31/35-$H_6$), 7.56-7.51 (m, $CH_{arom}$, 15/18/22/23/27/30/36/37-$H_8$), 7.63 (m, $CH_{arom}$, 14/24/26/38-$H_4$), 7.93 (dd, $CH_{arom}$, 7/10-$H_2$), 8.65 (s, $CH_{arom}$, 6/11-$H_2$), 8.87 (s, $CH_{arom}$, 5/12-$H_2$) ppm.

$^3J_{33,cis-34}$=17.6 Hz, $^3J_{33,cis-34}$=10.8 Hz.

$^{13}$C-NMR (125 MHz, $CDCl_3$, 300 K): δ=114.49 (33-C), 126.33 (8/9-C), 127.07-127.53 (6/11/15/18/22/23/27/30/31/35/36/37-C), 128.04 (20-C), 128.15 (5/12-C), 128.62 (7/10-C), 129.20 (19/21-C), 130.70-130.66 (14/24/26/38-C), 132.32 (5'11'-C), 132.63 (6'10'-C), 136.69 (33-C), 137.41 (32-C), 137.71 (1'/4'-C), 138.44-138.42 (13/25-C), 139.98 (29-C), 140.70 (17-C), 142.23-141.71 (16/28-C), 154.24-154.20 (2/3-C) ppm.

EI-MS: m/z=560 (M⁺)

Example 16—HOMO- and LUMO-Energies

For a number of the organic binders of the present application the orbital energies (HOMO=highest occupied molecular orbital, LUMO=lowest unoccupied molecular orbital) were determined by cyclic voltammetry. For pyrazino[2,3-b]phenazines only the energy of the LUMO could be determined by cyclic voltammetry. In this case the data of the optical bandgap, which was obtained from UV/VIS spectra, was used together with the LUMO-energy to calculate the HOMO-energy (these values are marked with *. Respective HOMO- and LUMO-energy values for a number of exemplary organic binders are indicated in Table 3.

TABLE 3

| | HOMO [eV] | LUMO [eV] |
|---|---|---|
| (structure 1) | −5.39 | −3.01 |
| (structure 2) | −6.07* | −3.54 |
| (structure 3) | −5.52 | −3.21 |

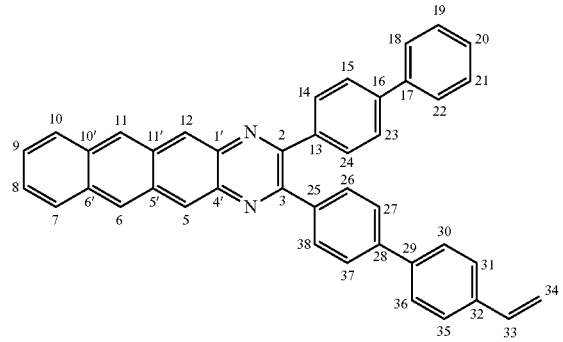 [SMILES: C=Cc1ccc(-c2ccc(-c3nc4cc5cc6ccccc6cc5cc4nc3-c3ccc(-c4ccccc4)cc3)cc2)cc1]

TABLE 3-continued

| | HOMO [eV] | LUMO [eV] |
|---|---|---|
| 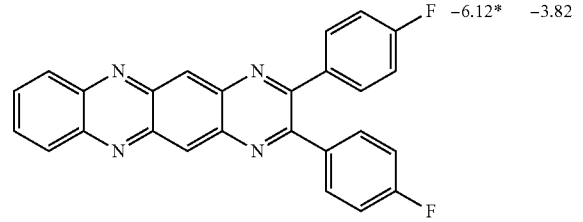 | −6.12* | −3.82 |
| 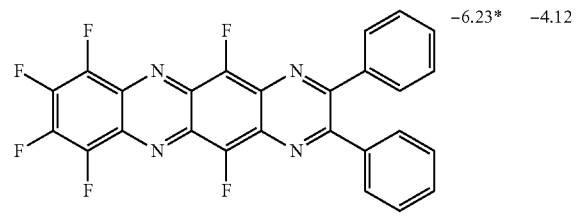 | −6.23* | −4.12 |

These results show that the present organic binders can be modified in such a way that their orbital energies match those of the inorganic semiconducting material, with which they are to be comprised in the semiconductor composition of the present application. The results also show that such adaptation, or "fine-tuning" can be performed over a broad range, thereby allowing to match a great variety of the inorganic semiconducting materials currently in use.

Example 17—Synthesis of a ZnO Nanoparticle Dispersion in an Organic Solvent

In a 250 ml three neck flask 13.5 g zinc acetate dihydrate were suspended in 35 ml methanol and warmed to 55° C., followed by the addition of 0.7 g potassium hydroxide (KOH). The resulting mixture was stirred for 40 min. Then a solution of 6 g KOH in 17.5 ml methanol was added dropwise to precipitate the particles. The resulting mixture was then stirred for 35 min at 0° C. in an ice bath and then centrifuged. Supernatant methanol was decanted and replaced with fresh methanol. The particles were re-suspended using sonication and centrifuged again. Supernatant methanol is removed and substituted with the solvent of choice for the dispersion, which generally was methanol, chloroform, dichloromethane ($CH_2Cl_2$), THF or 2-methoxyethanol. The ZnO nanoparticles were washed four times by re-suspending in the solvent of choice, centrifuging, decanting the supernatant solvent and replacing with fresh solvent of choice.

After drying at 100° C. ZnO nanoparticles of a methanolic dispersion were analyzed by TGA as described in detail in the test methods and found to consist of 95.2 wt % ZnO, respectively.

Example 18—Synthesis of an Aqueous ZnO Nanoparticle Dispersion

In a 250 ml three neck flask 13.5 g zinc acetate dihydrate were suspended in 35 ml methanol and warmed to 55° C., followed by the addition of 0.7 g potassium hydroxide (KOH). The resulting mixture was stirred for 40 min. Then a solution of 6 g KOH in 17.5 ml methanol was added dropwise to precipitate the particles. The resulting mixture was then stirred for 35 min at 0° C. in an ice bath and then centrifuged. Supernatant methanol was decanted and replaced with fresh methanol. The particles were re-suspended in methanol using sonication and centrifuged again. The particles were again re-suspended in 30 ml methanol and filled into a dialysis tube (Roth ZelluTrans with a nominal filter rate of 6,000 and a molecular weight cut-off (MWCO) of 8,000 to 10,000 and dialyzed against distilled water for 17 hours and after replacement of the water with fresh distilled water for another hour. A dispersion of ZnO-nanoparticles in water was obtained.

Ater drying at 100° C. ZnO nanoparticles of the aqueous dispersion were analyzed by TGA and found to consist of 97.4 wt % ZnO.

Example 19—Transistor Fabrication and Data with an Aqueous ZnO Dispersion

Two sets of thin film transistors 100 as schematically shown in FIG. 1 were fabricated on Si substrates/gate electrodes 101 (i.e. the substrates served at the same time as gate electrodes) with $SiO_2$ coating 102 having a thickness of 90 nm with photolithographically defined Au/ITO source and drain electrodes 103a and 103b, each having a thickness of 40 nm. An aqueous ZnO nanoparticle dispersion was applied to the substrate by spin coating and subsequently heated to a temperature of 250° C. for 10 min under an atmosphere of nitrogen to remove residual solvent to form a semiconducting layer 104.

Figure 2:
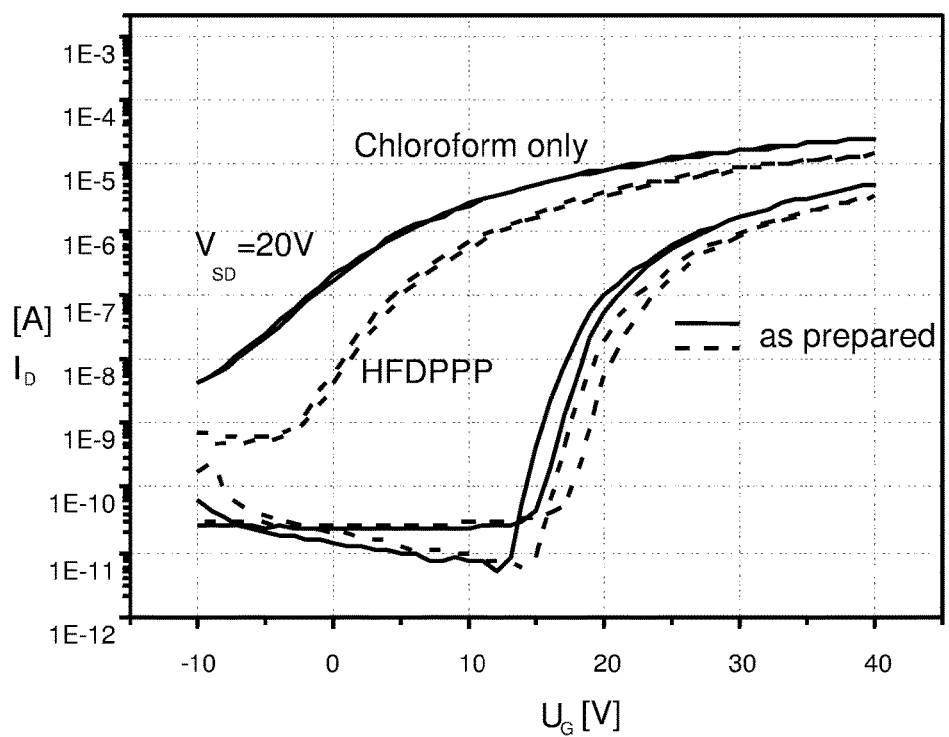
FIG. 2 shows the performance curves of the thin film transistor of Example 19.

For the two sets of devices obtained at this stage, performance was determined resulting in the bottom curves shown in FIG. 2, with respective values for charge mobility μ, threshold voltage $V_{th}$, onset voltage $V_{on}$ and $I_{on}/I_{off}$ ratio indicated in Table 4 in the row labeled "Untreated device".

Subsequently, the first set of devices, serving as comparative examples, was prepared by performing three times an infiltration step, wherein each time chloroform only was dripped onto the ZnO layer, heated to 150° C. fir 10 min under nitrogen and device performance determined, resulting in the dashed curves on top in FIG. 2, with respective values for charge mobility μ, threshold voltage $V_{th}$, onset voltage $V_{on}$ and $I_{on}/I_{off}$ ratio indicated in Table 4 in the row labeled "Chloroform only".

The second set of devices was prepared by performing three times an infiltration step, wherein each time a solution of HFDPPP in chloroform (1 mg $ml^{-1}$) was dripped onto the ZnO layer, heated to 150° C. for 10 min under nitrogen and device performance determined, resulting in the continuous curves on top in FIG. 2, with respective values for charge mobility μ, threshold voltage $V_{th}$, onset voltage $V_{on}$ and $I_{on}/I_{off}$ ratio indicated in Table 4 in the row labeled "Chloroform+HFDPPP".

TABLE 4

| | μ [$cm^2 V^{-1} s^{-1}$] | $V_{th}$ [V] | $V_{on}$ [V] | $I_{on}/I_{off}$ |
|---|---|---|---|---|
| Untreated device | 2.6 · $10^{-3}$ | 15.0 | 14 | 10,000 |
| Chloroform only | 3.0 · $10^{-3}$ | 0 | −10 | 8,700 |
| Untreated device | 2.0 · $10^{-3}$ | 17.0 | 16 | 10,000 |
| Chloroform + HFDPPP | 1.9 · $10^{-3}$ | 3.2 | −2 | 63,000 |

Example 20—Transistor Fabrication and Data for an Methanolic ZnO Dispersion

Thin firm transistors were produced and their performance measures as indicated for Example 19, except that a methanolic ZnO dispersion was used.

Figure 3:
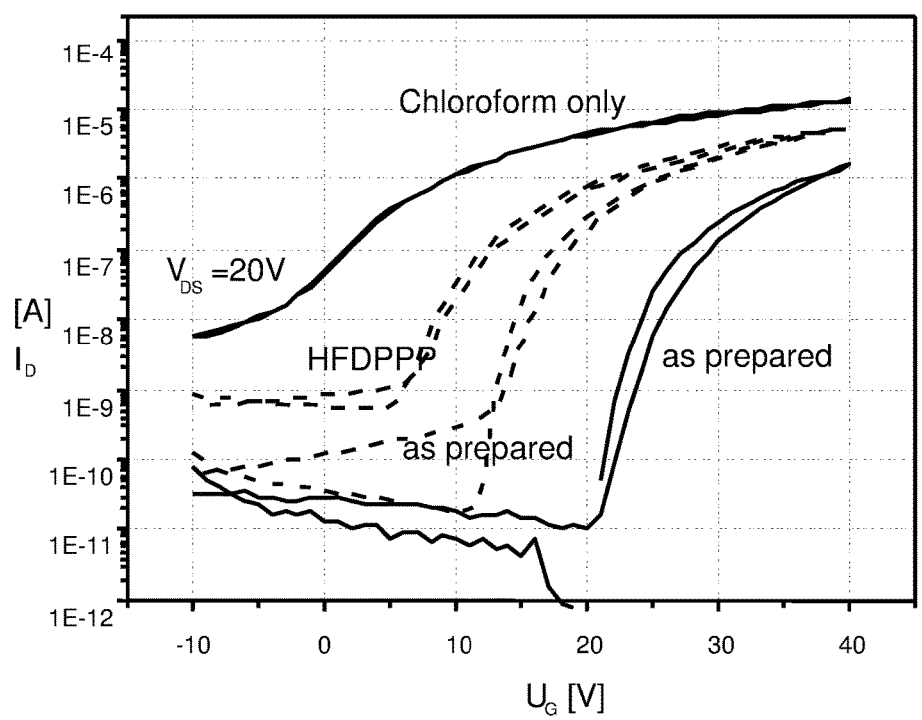
FIG. 3 shows the performance curves of the thin film transistor of Example 20.

The respective performance curves are shown in FIG. 3 and the respective data is indicated in Table 5.

TABLE 5

|  | μ [cm² V⁻¹ s⁻¹] | $V_{th}$ [V] | $V_{on}$ [V] | $I_{on}/I_{off}$ |
|---|---|---|---|---|
| Untreated device | 1.1 · 10⁻³ | 24.2 | 20 | 31,000 |
| Chloroform only | 1.5 · 10⁻³ | 3.3 | −5 | 2,700 |
| Untreated device | 1.3 · 10⁻³ | 17.6 | 13 | 61,000 |
| Chloroform + HFDPPP | 1.1 · 10⁻³ | 9.0 | 5 | 14,500 |

Generally stated the results obtained in accordance with the present application clearly show that impregnation of an inorganic semiconductor material with an organic binder as defined in the present application has a surprisingly strong influence on the properties of the respective thin film transistor. In particular it is surprising that the $I_{on}/I_{off}$ ratio could be significantly improved while at the same time shifting the threshold voltage close to the desired value of 0.

The invention claimed is:

1. Semiconductor composition comprising an inorganic semiconducting material and an organic binder, said organic binder being of formula (I)

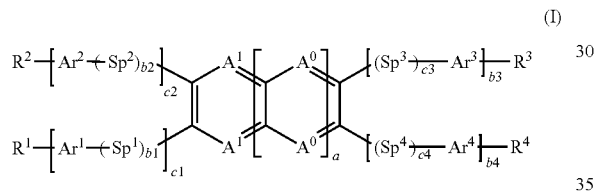

with a being at each occurrence independently of any other an integer selected from the group consisting of 1, 2, 3, 4, 5, 6 and 7, $A^0$ and $A^1$ being at each occurrence independently of each other either C—$R^5$ or N, provided that at least one of the $A^0$ and $A^1$ is N, b1, b2, b3, b4, c1, c2, c3 and c4 each being at each occurrence independently of the other 0 or 1, $Sp^1$, $Sp^2$, $Sp^3$ and $Sp^4$ being at each occurrence independently of the other selected from the group consisting of formulae (III-a) to (III-h)

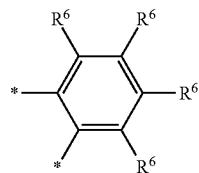 (III-a)

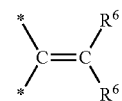 (III-b)

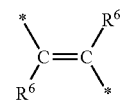 (III-c)

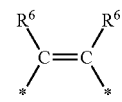 (III-d)

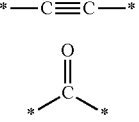 (III-e)

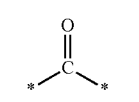 (III-f)

(III-g)

*—C≡C—*

(III-h)

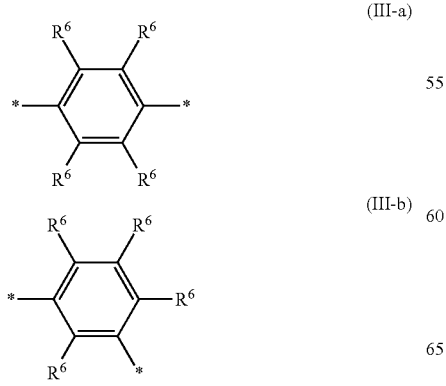

$Ar^1$, $Ar^2$, $Ar^3$ and $Ar^4$ being at each occurrence independently of the other selected from formulae (IV-a), (IV-b) or (IV-c)

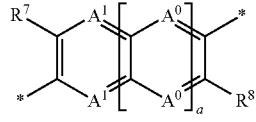 (IV-a)

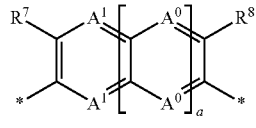 (IV-b)

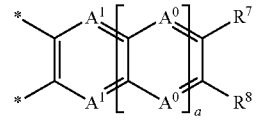 (IV-c)

wherein $R^1$, $R^2$, $R^3$, $R^4$, $R^7$, $R^8$ and—if present—$R^5$ and $R^6$ are at each occurrence independently of each other a group $R^A$ or a group $R^B$, provided that at least one, of $R^1$, $R^2$, $R^3$, $R^4$, $R^7$, $R^8$ and—if present—$R^5$ is a group $R^A$ with * denoting the respective bonds to the respective group $Sp^1$, $Sp^2$, $Sp^3$ or $Sp^4$ or—if such is not present—to the central unit of formulae (IV-a), (IV-b) or (IV-c), to the respective group $R^1$, $R^2$, $R^3$ or $R^4$ and to substituents $R^7$ and $R^8$;

$R^A$ being at each occurrence independently selected from the group consisting of (i) H, F, Br, Cl, —CN, —CH₂Br, —CH₂OR°, —NC, —NCO, —NCS, —OCN, —SCN, —C(O)NR°R°°, —C(O)X°, —C(O)R°, —C(O)R°—OR°°, —NR°R°°, —PR°R°°, —O—P(OR°)(OR°°), —O—

PH(O)—OR$^o$, —SH, —SR$^o$, —S(O)R$^o$, —SO$_3$H, —SO$_2$R$^o$, —SO$_3$R$^o$, —NO$_2$, —SF$_5$, —C≡C—R$^o$, —CR$^o$=CR$^{oo}$R$^{ooo}$,
(ii) fluorinated alkyl having from 1 to 40 carbon atoms,
(iii) alkyl or fluorinated alkyl having from 1 to 40 carbon atoms, wherein two adjacent carbon atoms are replaced by —CR$^o$=CR$^{oo}$— or —C≡C—,
(iv) alkyl or fluorinated alkyl having from 1 to 40 carbon atoms, wherein one or more carbon atoms are replaced by a heteroatom or heteroatom group,
(v) aryl having from 6 to 30 carbon ring atoms,
(vi) heteroaryl having from 5 to 30 ring atoms, wherein said aryl and heteroaryl may be unsubstituted or substituted with one or more groups R$^S$, and wherein said alkyl and fluorinated alkyl may be substituted with one or more groups selected from the group consisting of R$^S$, aryl and heteroaryl, R$^B$ being at each occurrence independently selected from the group consisting of
(i) H, —SiR$^o$R$^{oo}$R$^{ooo}$,
(ii) alkyl having from 1 to 40 carbon atoms,
(iii) alkoxy having from 1 to 39 carbon atoms,
(iv) —(CH$_2$)$_d$—R$^9$, wherein d is an integer of from 1 to 5 and R$^9$ is selected from the group consisting of
  (a) —SiR$^o$R$^{oo}$R$^{ooo}$, —C≡C—SiR$^o$R$^{oo}$R$^{ooo}$,
  (b) alkyl having from 1 to 19 carbon atoms,
  (c) alkyl having from 1 to 19 carbon atoms, wherein two adjacent carbon atoms are replaced by CR$^o$=CR$^{oo}$— or —C≡C—,
  (d) alkyl having from 1 to 19 carbon atoms, wherein one or more carbon atoms are replaced by a heteroatom or heteroatom group,
  (e) aryl having from 6 to 30 carbon ring atoms, and
  (f) heteroaryl having from 5 to 30 ring atoms, wherein said aryl and heteroaryl may be unsubstituted or substituted with one or more groups R$^S$, and wherein said alkyl and fluorinated alkyl may be substituted with one or more groups selected from the group consisting of R$^S$, aryl and heteroaryl, R$^o$, R$^{oo}$, and R$^{ooo}$ being at each occurrence independently of each other selected from the group consisting of H, F, C$_{1-40}$ organyl or organoheteryl, and substituted C$_{1-40}$ organyl or organoheteryl;

X$^o$ being at each occurrence independently selected from the group consisting of F, Cl, Br and I; and R$^8$ being at each occurrence independently selected from the group consisting of alkyl having from 1 to 30 carbon atoms, halogenated alkyl having from 1 to 30 carbon atoms, aryl having from 6 to 30 carbon ring atoms, aryl having from 6 to 30 carbon ring atoms substituted with at least one group independently selected from the group consisting of F, Cl, Br, I, alkyl having from 1 to 30 carbon atoms and halogenated alkyl having from 1 to 30 carbon atoms, heteroaryl having from 1 to 30 ring atoms, heteroaryl having from 1 to 30 ring atoms substituted with at least one group independently selected from the group consisting of F, Cl, Br, I, alkyl having from 1 to 30 carbon atoms and halogenated alkyl having from 1 to 30 carbon atoms.

2. Semiconductor composition according to claim 1, wherein b1, b2, b3, b4 c1, c2, c3 and c4 are selected such that one or more of the following conditions are met, provided that they are not mutually exclusive
(i) b1 and c1 are identical and are 0 or 1,
(ii) b2 and c2 are identical and are 0 or 1,
(iii) b3 and c3 are identical and are 0 or 1,
(iv) b4 and c4 are identical and are 0 or 1, and
(v) the sum of c1, c2, c3 and c4 (i.e. c1+c2+c3+c4) is at most 3.

3. The semiconductor composition according to claim 2, wherein the sum of c1, c2, c3 and c4 (i.e. c1+c2+c3+c4) is 0.

4. Semiconductor composition according to claim 1, wherein at least two of R$^1$, R$^2$, R$^3$, R$^4$, R$^7$, R$^8$ and—if present—R$^5$ is a group R$^A$.

5. Semiconductor composition of claim 1, wherein said organic binder is selected from the group consisting of formulae (I-1) to (I-16)

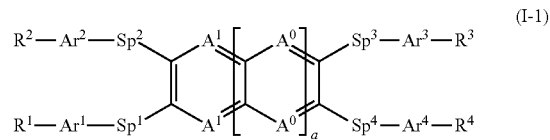
(I-1)

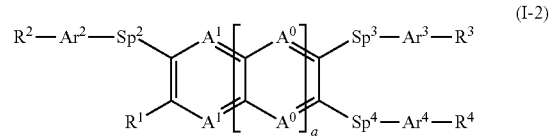
(I-2)

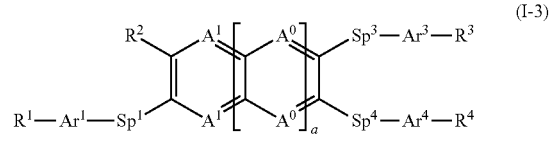
(I-3)

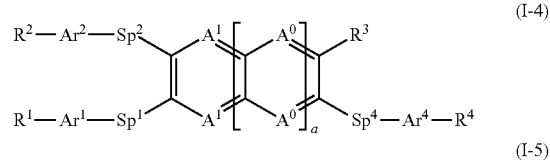
(I-4)

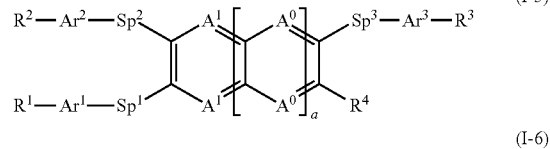
(I-5)

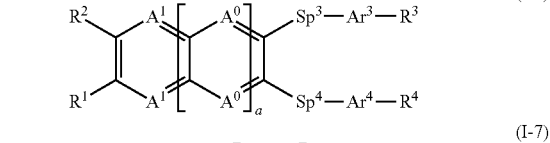
(I-6)

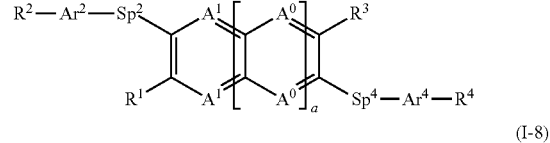
(I-7)

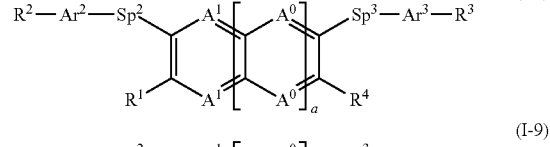
(I-8)

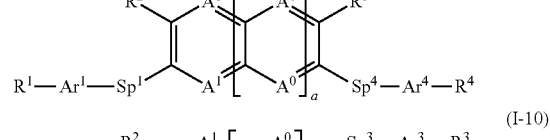
(I-9)

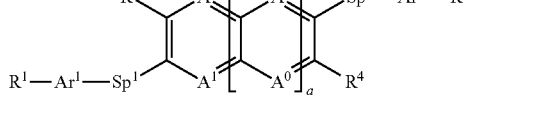
(I-10)

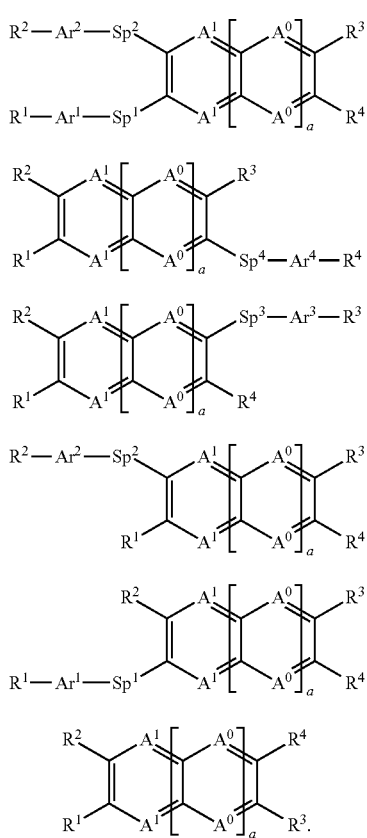

(I-11)

(I-12)

(I-13)

(I-14)

(I-15)

(I-16)

6. Semiconductor composition according to claim 1, wherein said organic binder is of formula (I-16)

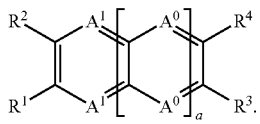

(I-16)

7. Semiconductor composition according to claim 6, wherein the organic binder is selected from the group consisting of the following formulae (I-16-b) and (I-16-c)

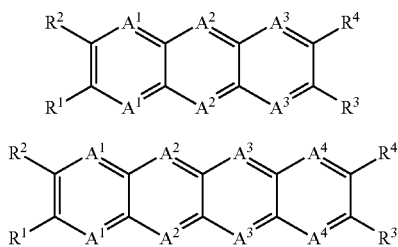

(I-16-b)

(I-16-c)

wherein $A^1$, $A^2$, $A^3$, $A^4$, $A^5$ and $A^6$ are at each occurrence independently of each other either C—$R^5$ or N, provided that at least one of the $A^1$, $A^2$, $A^3$, $A^4$, $A^5$ and $A^6$ is N.

8. Semiconductor composition according to claim 7, wherein the organic binder of formulae (I-16-b) or (I-16-c) is a binder of formulae (I-16-b-1), (I-16-b-2), (I-16-c-1), (I-16-c-2) or (I-16-c-3), wherein $A^1$, $A^2$, $A^3$ and $A^4$ are defined as

| Formula    | $A^1$   | $A^2$   | $A^3$   | $A^4$ |
|------------|---------|---------|---------|-------|
| (I-16-b-1) | C-$R^5$ | N       | C-$R^5$ | —     |
| (I-16-b-2) | N       | C-$R^5$ | B       | —     |
| (I-16-c-1) | C-$R^5$ | C-$R^5$ | C-$R^5$ | N     |
| (I-16-c-2) | C-$R^5$ | N       | C-$R^5$ | N     |
| (I-16-c-3) | N       | C-$R^5$ | N       | C-$R^5$ |

9. Semiconductor composition according to claim 1, wherein the organic binder is selected from the group consisting of the following formulae (I-16-a) to (I-16-e)

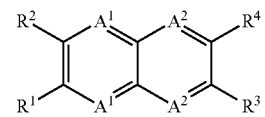

(I-16-a)

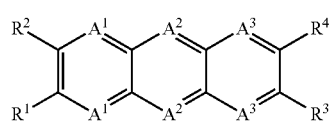

(I-16-b)

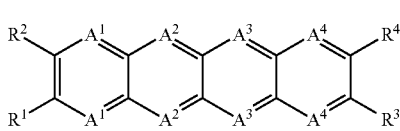

(I-16-c)

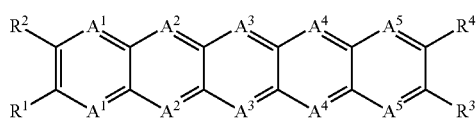

(I-16-d)

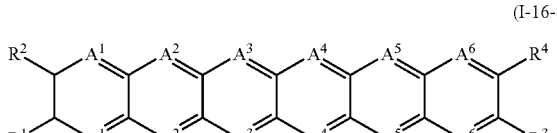

(I-16-e)

wherein $A^1$, $A^2$, $A^3$, $A^4$, $A^5$ and $A^6$ are at each occurrence independently of each other either C—$R^5$ or N, provided that at least one of the $A^1$, $A^2$, $A^3$, $A^4$, $A^5$ and $A^6$ is N.

10. Semiconductor composition according to claim 9, wherein in any of formulae (I-16-a) to (I-16-e) whichever of $A^2$, $A^3$, $A^4$, $A^5$ and $A^6$ is adjacent to $R^3$ is N or whichever of $A^0$, $A^2$, $A^3$, $A^4$, $A^5$ and $A^6$ is adjacent to $R^4$ is N or both are N.

11. Semiconductor composition according to claim 9, wherein in any of formulae (I-16-a) to (I-16-e) the respective groups $A^1$, $A^2$, $A^3$, $A^4$, $A^5$ and $A^6$ bound to the same fusion atom are different from each other.

12. Semiconductor composition according to claim 1, wherein $R^4$ is F or fluorinated alkyl.

13. Semiconductor composition according to claim 1, wherein the organic binder is selected from the group consisting of the following formulae (V-a) to (V-h)

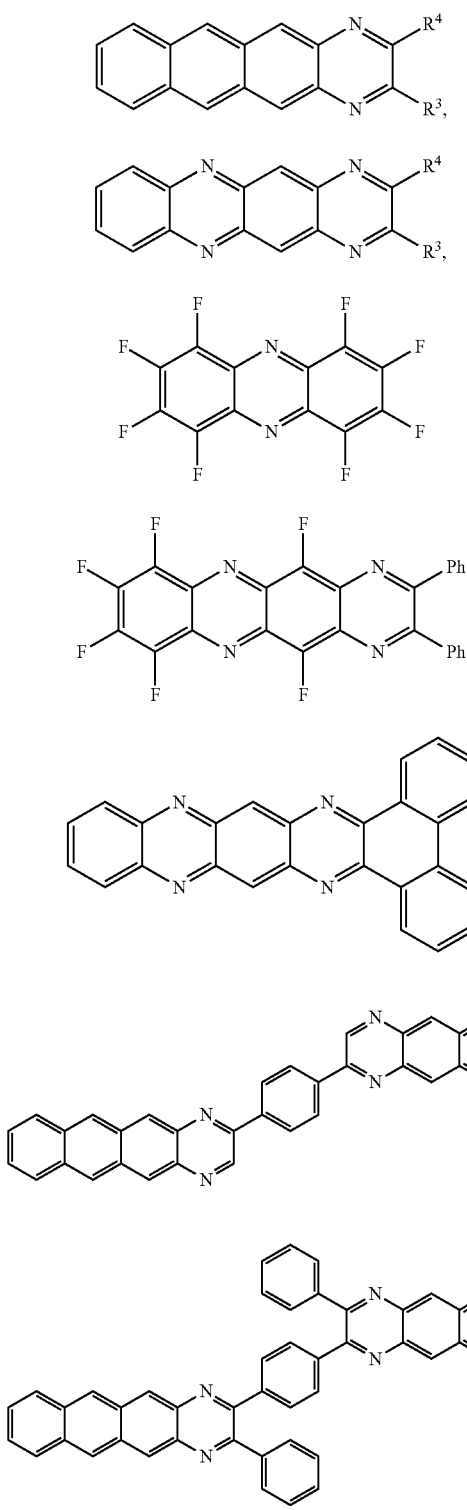

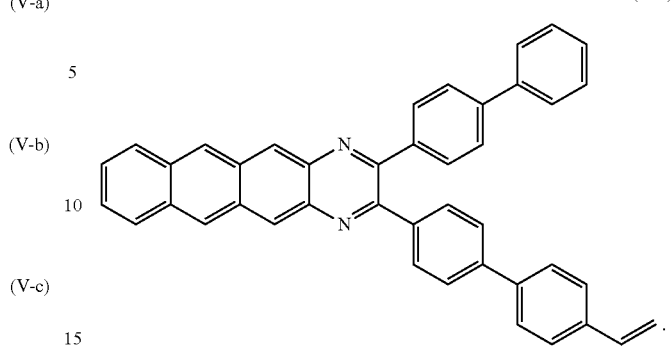

14. Semiconductor composition according to claim 1, wherein the inorganic semiconducting material is an inorganic semiconducting nanoparticle material.

15. Semiconductor composition according to claim 1, wherein the inorganic semiconducting material is an n-type semiconducting material.

16. Semiconductor composition according to claim 1, wherein the inorganic semiconducting material is selected from the group consisting of metal oxides, metal sulfides, metal selenides and metal tellurides.

17. Organic electronic device comprising a semiconducting layer consisting of the semiconductor composition of claim 1.

18. The semiconductor composition according to claim 1 wherein $R^4$ is at each occurrence independently an alkyl or fluorinated alkyl having from 1 to 40 carbon atoms, wherein one or more, non-adjacent carbon atoms are replaced by a heteroatom or heteroatom group.

19. The semiconductor composition according to claim 1 wherein A is at each occurrence independently an alkyl or fluorinated alkyl having from 1 to 40 carbon atoms; wherein one or more, non-adjacent carbon atoms are replaced by a heteroatom or heteroatom group.

20. Process for the production of an organic electronic device, said process comprising the steps of
(A-i) providing a dispersion of an inorganic semiconducting nanoparticle material in a dispersant;
(A-ii) applying said dispersion to a substrate;
(A-iii) removing said dispersant, thus obtaining a layer of an inorganic semiconducting nanoparticles material;
(A-iv) providing a solution of an organic binder of claim 1 in a solvent;
(A-v) applying said solution to the layer of an inorganic semiconducting nanoparticle material obtained in step (A-iii); and
(A-vi) removing said solvent,
or said process comprising the steps of
(B-i) mixing an inorganic semiconducting nanoparticles material, an organic binder and a solvent to obtain a semiconductor formulation;
(B-ii) applying said semiconductor formulation to a substrate; and
(B-iii) removing said solvent,
to obtain a semiconducting layer.

* * * * *